(12) United States Patent
Saji et al.

(10) Patent No.: US 8,980,220 B2
(45) Date of Patent: Mar. 17, 2015

(54) MOLECULAR PROBE FOR IMAGING OF PANCREATIC ISLETS AND USE OF THE SAME

(75) Inventors: Hideo Saji, Kyoto (JP); Nobuya Inagaki, Kyoto (JP); Kentaro Toyoda, Kyoto (JP); Hiroyuki Kimura, Kyoto (JP); Konomu Hirao, Kyoto (JP); Kenji Nagakawa, Kyoto (JP); Hirokazu Matsuda, Kyoto (JP)

(73) Assignees: Kyoto University, Kyoto (JP); ARKRAY, Inc., Kyoto (JP)

( * ) Notice: Subject to any disclaimer, the term of this patent is extended or adjusted under 35 U.S.C. 154(b) by 792 days.

(21) Appl. No.: 12/964,486

(22) Filed: Dec. 9, 2010

(65) Prior Publication Data

US 2011/0206605 A1 Aug. 25, 2011

Related U.S. Application Data

(60) Provisional application No. 61/285,293, filed on Dec. 10, 2009, provisional application No. 61/350,732, filed on Jun. 2, 2010, provisional application No. 61/388,948, filed on Oct. 1, 2010.

(30) Foreign Application Priority Data

Dec. 10, 2009 (JP) ................................. 2009-280396
Jun. 1, 2010 (JP) ................................. 2010-125983

(51) Int. Cl.
*C07K 14/605* (2006.01)
*G01N 33/74* (2006.01)
*A61K 51/08* (2006.01)

(52) U.S. Cl.
CPC .............. *G01N 33/74* (2013.01); *A61K 51/088* (2013.01); *C07K 14/605* (2013.01)
USPC .............. 424/1.69; 514/1.1; 435/29; 530/324

(58) Field of Classification Search
None
See application file for complete search history.

(56) References Cited

U.S. PATENT DOCUMENTS 6,821,949 B2 * 11/2004 Bridon et al. .................. 514/5.9
2009/0180953 A1 7/2009 Gotthardt et al.

FOREIGN PATENT DOCUMENTS

| EP | 1867634 | 12/2007 |
|---|---|---|
| EP | 2418216 A1 | 2/2012 |
| JP | 09-292466 | 11/1997 |
| JP | 2008-511557 | 4/2008 |
| WO | WO 2004/035744 | 4/2004 |
| WO | WO 2006/107106 | 10/2006 |

OTHER PUBLICATIONS

Martin et al., Diabetes, 2009, 58(2), 318-328.*
Gotthardt et al., Regulatory Peptides, 2006, 137, 162-167.*
Runge et al., Biochemistry, 2007, 46(19) 5830-5840.*
Goke et al., J. Bio. Chem., 1993, 268(26) 19650-19655.*
Arkray, Inc., "Leading research on molecular imaging device for supporting treatment of malignant tumor, etc. / development of method for ultra-early diagnosis of diabetes by noninvasive in-vivo pancreatic islets imaging", Interim report of Heisei 19 (2007) fiscal year, out of Heisei 19 to 20 (2007 to 2008) years (Sep. 19, 2008) (partial (pp. 1, 5) translation provided).
S. Al-Sabah et al., "The positive charge at Lys-288 of the glucagon-like peptide-1 (GLP-1) receptor is important for binding the N-terminus of peptide agonists", FEBS Letters 553: 342-346 (2003).
M. Behe et al., "Are radiolabeled GLP-1 receptor antagonists useful for scintigraphy?", 2009 SNM Annual Meeting, abstract, Oral Presentations No. 327 (May 2009).
M. Brom et al., "$^{68}$Ga-labelled exendin-3, a new agent for the detection of insulinomas with PET", Eur. J. Nucl. Med. Mol. Imaging 37: 1345-1355 (2010).
E. Christ et al., "Glucagon-Like Peptide-1 Receptor Imaging for Localization of Insulinomas", J. Clin. Endocrinol Metab. 94(11): 4398-4405 (Nov. 2009).
R. Göke et al., "Exendin-4 is a High Potency Agonist and Truncated Exendin-(9-39)-amide an Antagonist at the Glucagon-like Peptide 1-(7-36)-amide Receptor of Insulin-secreting β-Cells", J. Biol. Chem. 268(26): 19650-19655 (1993).
M. Gotthardt et al., "Use of the incretin hormone glucagon-like peptide-1 (GLP-1) for the detection of insulinomas: initial experimental results", European Journal of Nuclear Medicine 29(5): 598-606 (May 2002).
M. Gotthardt et al., "A new technique for in vivo imaging of specific GLP-1 binding sites: First results in small rodents", Regulatory Peptides 137: 162-167 (2006).

(Continued)

*Primary Examiner* — James H Alstrum Acevedo
*Assistant Examiner* — Roy Teller
(74) *Attorney, Agent, or Firm* — Morgan, Lewis & Bockius LLP

(57) ABSTRACT

A molecular probe for use in imaging of pancreatic islets is provided. The molecular probe comprises a polypeptide represented by the following formula (1), (2), or (3), or a polypeptide having homology with the foregoing polypeptide,

```
                                                    (SEQ ID NO. 1)
Z-HGEGTFTSDLSXQMEEEAVRLFIEWLKNGGPSSGAPPPS-NH₂  (1)

(SEQ ID NO. 2)
Z-HGEGTFTSDLSKQMEEEAVRLFIEWLXNGGPSSGAPPPS-NH₂  (2)

(SEQ ID NO. 3)
B-HGEGTFTSDLSKQMEEEAVRLFIEWLKNGGPSSGAPPPS-NH₂  (3)
``` where, in the formulae (1) and (2), "X" represents a lysine residue, an amino group of a side chain of the lysine residue being labeled with a radioactive nuclide, and "Z—" indicates that an α-amino group at an N-terminus is not modified, or is modified with a modifying group having no electric charge; in the formula (3), "B—" indicates that an α-amino group at an N-terminus is labeled with a radioactive nuclide; and in the formulae (1), (2), and (3), "—NH₂" indicates that a carboxyl group at a C-terminus is amidated.

25 Claims, 10 Drawing Sheets

(56) References Cited

OTHER PUBLICATIONS

B.D. Green et al., "Chronic treatment with exendin(9-39)amide indicates a minor role for endogenous glucagon-like peptide-1 in metabolic abnormalities of obesity-related diabetes in ob/ob mice", J. Endocrinol. 185: 307-317 (2005).

K. Hirao, "Leading research on molecular imaging device for supporting treatment of malignant tumor, etc. / Development of method for ultra-early diagnosis of diabetes by noninvasive in-vivo pancreatic islet imaging", Interim report of Heisei 20 (2008) Fiscal Year, out of Heisei 19 to 20 (2007-2008) years (May 20, 2009) (partial (pp. 1, 2) translation provided).

N. Inagaki, "Research on development of method for ultra-early diagnosis of diabetes by noninvasive in-vivo pancreatic islet imaging", Heisei 19 (2007) Fiscal Year Overview Research Report, Research Project for Medical Equipment Development Promotion, Grants-in-Aid for Scientific Research from Ministry of Health, Labor and Welfare (Apr. 20, 2008) (partial (pp. 1-7, 10-15, 24, 25) translation provided).

N. Inagaki, "Research on development of method for ultra-early diagnosis of diabetes by noninvasive in-vivo pancreatic islet imaging", Heisei 20 (2008) Fiscal Year Overview Research Report, Research Project for Medical Equipment Development Promotion, Grants-in-Aid for Scientific Research from Ministry of Health, Labor and Welfare (Apr. 21, 2009) (partial (pp. 1-7, 10-17, 23, 24) translation provided).

N. Inagaki, "Development of method for ultra-early diagnosis of diabetes by noninvasive in-vivo pancreatic islet imaging", Research of New Medical Devices 13, 72-73 (Mar. 25, 2008) (partial (pp. 72, 73) translation provided).

H. Kimura et al., "Development of in vivo imaging agents targeting glucagon-like peptide-1 receptor (GLP-1R) in pancreatic islets", 2009 SNM Annual Meeting, abstract, Oral Presentations No. 326 (May 2009).

The MICAD Research Team, "$^{111}$In-Diethylenetriaminepentaacetic acid-aminohexanoic acid-Lys$^{40}$-exendin-4".

E. Mukai et al., "Non-invasive imaging of pancreatic islets targeting glucagon-like peptide-1-receptors", 44th EASD Annual Meeting (Rome), abstract, Presentation No. 359 (2008).

E. Mukai et al., "GLP-1 receptor antagonist as a potential probe for pancreatic B-cell imaging", Biochem. Biophys. Res. Commun. 389(3): 523-526 (2009).

J. W. Neidigh et al., "Exendin-4 and Glucagon-like peptide-1: NMR Structural Comparisons in the Solution and Micelle-Associated States", Biochemistry 40: 13188-13200 (2001).

U. Ritzel et al., "A synthetic glucagon-like peptide-1 analog with improved plasma stability", Journal of Endocrinology 159: 93-102 (1998).

J. Schirra et al., "Exendin(9-39)amide Is an Antagonist of Glucagon-like Peptide-1)7-36)amide in Humans", J. Clin. Invest. 101(7): 1421-1430 (Apr. 1998).

G. Vaidyanathan et al., "Protein Radiohalogenation: Observations on the Design of N-Succinimidyl Ester Acylation Agents", Bioconjug. Chem. 1(4), 269-273 (Jul. 1990).

G. Vaidyanathan et al., "Radioiodination of Proteins Using N-Succinimidyl 4-Hydroxy-3-iodobenzoate", Bioconjug. Chem. 4(1), 78-84 (Jan. 1993).

A. Wicki et al., "[Lys$^{40}$(Ahx-DTPA-$^{111}$In)NH$_2$]-Exendin-4 Is a Highly Efficient Radiotherapeutic for Glucagon-Like Peptide-1 Receptor-Targeted Therapy for Insulinoma", Clin. Cancer Res. 13(12): 3696-3705 (Jun. 15, 2007).

D. Wild et al., "[Lys$^{40}$(Ahx-DTPA-$^{111}$In)NH$_2$]Exendin-4, a Very Promising Ligand for Glucagon-like Peptide-1 (GLP-1) Receptor Targeting", J. Nucl. Med. 47: 2025-2033 (2006).

Office Action issued in corresponding European Patent Application No. 10836003.3 dated Dec. 10, 2013.

Office Action issued in corresponding Japanese Patent Application No. 2011-507740 dated Oct. 29, 2013.

Office Action issued in corresponding European Patent Application No. 10836003.3 dated May 6, 2014.

Extended European Search Report issued in corresponding European Patent Application No. 10836003.3 dated Apr. 15, 2013.

Al Sabah et al., "A model for receptor-peptide binding at the glucagon-like peptide-1 (GLP-1) receptor through the analysis of truncated ligands and receptors," British Journal of Pharmacology, 140: 339-346 (2003).

* cited by examiner

MOLECULAR PROBE FOR IMAGING OF PANCREATIC ISLETS AND USE OF THE SAME

This application claims priority to Provisional Application No. 61/285,293, filed Dec. 10, 2009; Provisional Application No. 61/350,732, filed Jun. 2, 2010; Provisional Application No. 61/388,948, filed Oct. 1, 2010; Japanese Application No. 2009-280396, filed Dec. 10, 2009 and Japanese Application No. 2010-125983, filed Jun. 1, 2010, each of which is hereby incorporated by reference in its entirety.

SEQUENCE LISTING SUBMISSION VIA EFS-WEB

A computer readable text file, entitled "068022-5019-SequenceListing.txt," created on or about Apr. 29, 2011 with a file size of about 17 kb contains the sequence listing for this application and is hereby incorporated by reference in its entirety.

BACKGROUND OF THE INVENTION

1. Field of the Invention

The present invention relates to a molecular probe for imaging of pancreatic islets, and the use of the same.

2. Description of Related Art

Today, the estimated number of type-II diabetics in Japan exceeds 8,800,000 according to the statistic in fiscal 2007, and has been increasing further continuously, as compared with fiscal 2002. As a measure against this increase, interventions for preventing diabetes from developing have been made based on the glucose tolerance test, resulting, however, in unsatisfactory effects. The cause is as follows: at such a borderline stage that functional abnormalities are found by the glucose tolerance test, disorders of pancreatic islets have already advanced to a high degree, and this stage possibly is too late as a time for starting interventions.

Recently, it has been reported at home and overseas that even in type-II diabetics the amount of pancreatic islets already has decreased upon the development, and it has been considered that a further decrease in pancreatic β-cells after the development is one of the resistance factors against treatment for type-II diabetics. Therefore, if the amount of pancreatic islets and/or the amount of pancreatic β-cells is detected, there is possibility for the clarification of pathogenesis, the ultra-early diagnosis, and the prevention of development of type-II diabetics. For this purpose, a technique for detecting the amount of pancreatic islets and/or the amount of pancreatic β-cells has been desired.

As a technique for detecting the amount of pancreatic islets and/or the amount of pancreatic β-cells, for example, a method for noninvasive quantification using a diagnostic imaging method, that is, a technique for noninvasive imaging of pancreatic islets, is being developed. For this, a probe that enables noninvasive imaging of pancreatic islets, preferably pancreatic β-cells, and noninvasive determination of the amount of pancreatic β-cells has been desired.

In designing a molecular probe for imaging of pancreatic islets, various target molecules in pancreatic cells, particularly functional proteins specific in the β-cells, are being researched. Among these, GLP-1R (glucagon-like peptide-1 receptor) is being researched as a target molecule; GLP-1R is distributed in pancreatic β-cells, and is a seven-transmembrane G protein coupled receptor.

As molecular probes for imaging that use GLP-1R as a target molecule, the following are researched: a peptide derivative of GLP-1 having a C-terminus to which a labeling molecule is bonded; a peptide derivative of exendin-3 having a C-terminus to which a labeling molecule is bonded; and a peptide derivative of exendin-4 having a C-terminus to which a labeling molecule is bonded (e.g., JP 2008-511557A).

Further, the following, for example, also are researched: a molecular probe obtained by labeling a derivative of exendin-4(9-39) with [$^{18}$F] fluorine (e.g., H. Kimura et al. Development of in vivo imaging agents targeting a glucagons-like peptide-1 receptor (GLP-1R) in pancreatic islets. 2009 SNM Annual Meeting, abstract, Oral Presentations No. 326); a molecular probe obtained by adding a lysine at a C-terminus of exendin-4, and labeling the exendin-4 with [$^{111}$In] indium via diethylenetriaminepentaacetic acid (DTPA) bonded to a residue of the added lysine (Lys$^{40}$(Ahx-DTPA-$^{111}$In)Exendin-4) (e.g., M. Gotthardt et al., "A new technique for in vivo imaging of specific GLP-1 binding sites": First results in small rodents, Regulatory Peptides 137 (2006) 162-267, and M. Beche et al., "Are radiolabeled GLP-1 receptor antagonists useful for scintigraphy?": 2009 SNM Annual Meeting, abstract, Oral Presentations No. 327); and a molecular probe obtained by adding a lysine at a C-terminus of exendin-4(9-39), and labeling the exendin-4(9-39) with [$^{111}$In] indium via diethylenetriaminepentaacetic acid bonded to a residue of the added lysine (Lys$^{40}$(Ahx-DTPA-$^{111}$In)Exendin-4(9-39)) (e.g., M. Beche et al., "Are radiolabeled GLP-1 receptor antagonists useful for scintigraphy?": 2009 SNM Annual Meeting, abstract, Oral Presentations No. 327).

However, a novel molecular probe for imaging of pancreatic islets is desired that enables noninvasive three-dimensional imaging of pancreatic islets.

SUMMARY OF THE INVENTION

The present invention provides a molecular probe for imaging of pancreatic islets that enables three-dimensional imaging of pancreatic islets.

The present invention relates to a molecular probe for use in imaging of pancreatic islets, the molecular probe comprising any one of the following polypeptides:

a polypeptide represented by the following formula (1), (2), or (3);

a polypeptide that is obtained by deletion, insertion, or substitution of one to several amino acids with respect to the polypeptide represented by the following formula (1), (2), or (3) and that is capable of binding to pancreatic islets; and a polypeptide that has a homology of 80% or higher with the amino acid sequence of the polypeptide represented by the following formula (1), (2), or (3) and that is capable of binding to pancreatic islets, (SEQ ID NO. 1)
Z-HGEGTFTSDLSXQMEEEAVRLFIEWLKNGGPSSGAPPPS-NH$_2$ (1)

(SEQ ID NO. 2)
Z-HGEGTFTSDLSKQMEEEAVRLFIEWLXNGGPSSGAPPPS-NH$_2$ (2)

(SEQ ID NO. 3)
B-HGEGTFTSDLSKQMEEEAVRLFIEWLKNGGPSSGAPPPS-NH$_2$ (3)

where
in the formulae (1) and (2),
"X" represents a lysine residue, an amino group of a side chain of the lysine residue being labeled with a radioactive nuclide, and "Z—" indicates that an α-amino group at an N-terminus is not modified, or is modified with a modifying group having no electric charge, in the formula (3), "B—" indicates that an α-amino group at an N-terminus is labeled with a radioactive nuclide, and in the formulae (1), (2), and (3), "—NH$_2$" indicates that a carboxyl group at a C-terminus is amidated.

Further, another aspect of the present invention relates to a precursor of a molecular probe for imaging, used for producing a molecular probe for imaging of the present invention, the precursor comprising any one of the following polypeptides:

a polypeptide represented by the following formula (4), (5), or (6);

a polypeptide that is obtained by deletion, insertion, or substitution of one to several amino acids with respect to the polypeptide represented by the following formula (4), (5), or (6) and that is capable of binding to pancreatic islets after being labeled and deprotected; and a polypeptide that has a homology of 80% or higher with the amino acid sequence of polypeptide represented by the following formula (4), (5), or (6) and that is capable of binding to pancreatic islets after being labeled and deprotected:

```
                                                (SEQ ID NO. 4)
*-HGEGTFTSDLSKQMEEEAVRLFIEWLK*NGGPSSGAPPPS-NH2  (4)

(SEQ ID NO. 5)
*-HGEGTFTSDLSK*QMEEEAVRLFIEWLKNGGPSSGAPPPS-NH2  (5)

(SEQ ID NO. 6)
 HGEGTFTSDLSK*QMEEEAVRLFIEWLK*NGGPSSGAPPPS-NH2  (6)
``` where in the formulae (4) and (5),

"*-" indicates that an α-amino group at an N-terminus is protected by a protecting group, or is modified with a modifying group having no electric charge, in the formulae (4), (5), and (6), "K*" indicates that an amino group of a side chain of a lysine is protected by a protecting group, and "—NH$_2$" indicates that a carboxyl group at a C-terminus is amidated.

Further, still another aspect of the present invention relates to a method for imaging of pancreatic islets that comprises detecting a signal of the above-described molecular probe for imaging of the present invention from an analyte to which the molecular probe has been administered.

Further, still another aspect of the present invention relates to a method for determining an amount of pancreatic islets, the method including detecting a signal of the above-described molecular probe for imaging of the present invention from an analyte to which the molecular probe has been administered, and calculating an amount of pancreatic islets from the detected signal of the molecular probe.

The present invention enables three-dimensional imaging of pancreatic islets, and preferably noninvasive three-dimensional imaging of pancreatic islets.

Figure 5:
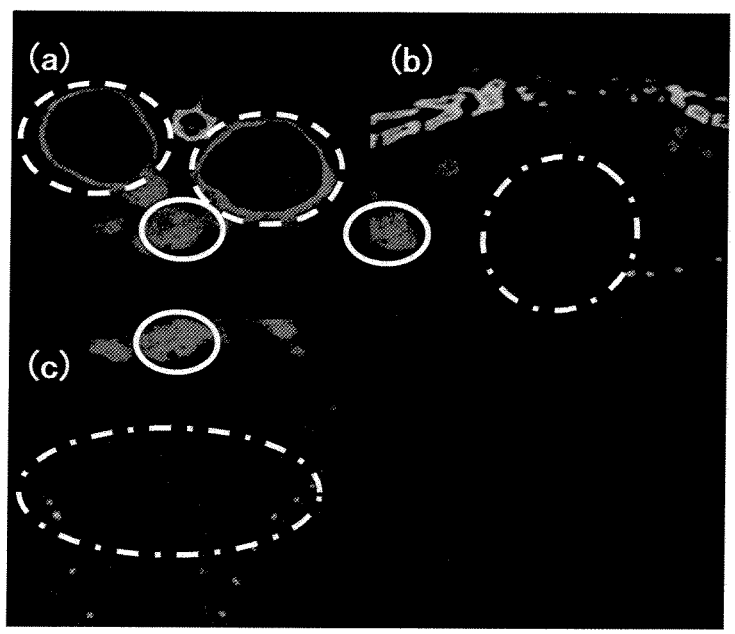

(a) to (c) of FIG. 5 are images showing exemplary results of three-dimensional imaging (PET imaging) using a molecular probe for imaging according to Example 2.

Figure 6A:
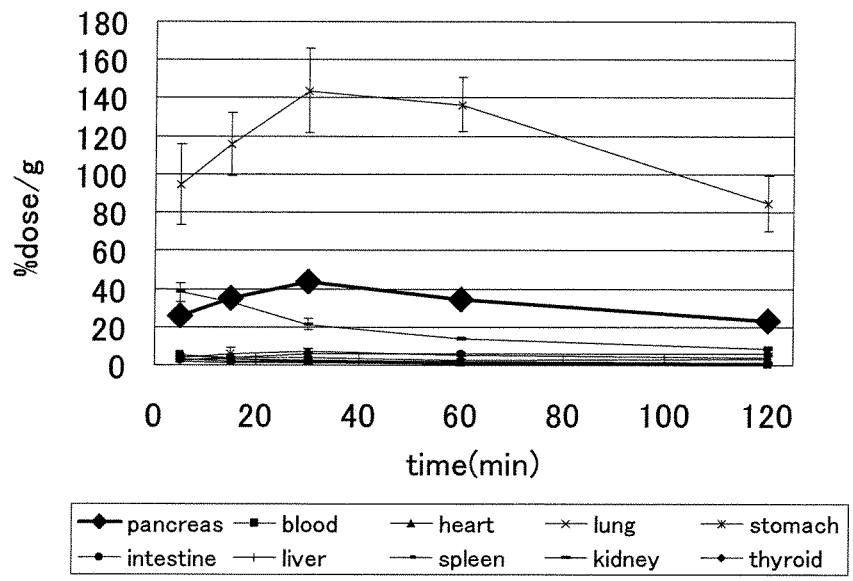
Figure 6B:
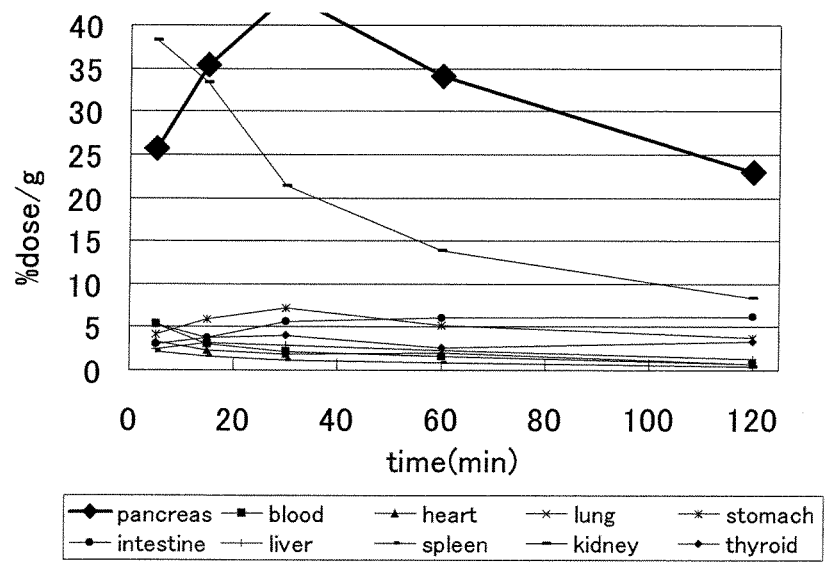

FIGS. 6A and 6B are graphs showing exemplary variations with time of biodistribution of a molecular probe for imaging according to Example 3.

FIG. 7 is a graph showing exemplary results of a blocking experiment using the molecular probe for imaging according to Example 3.

Figure 8:
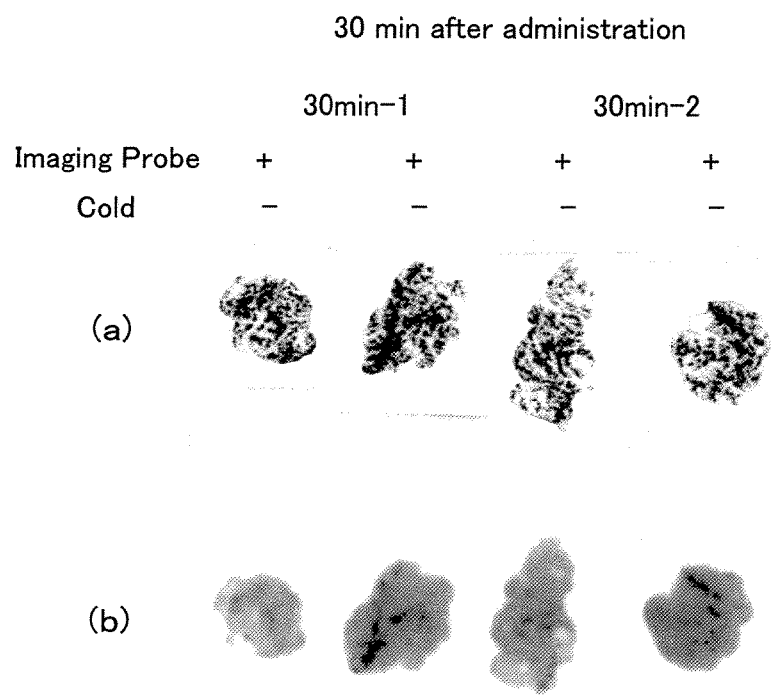

FIG. 8 shows images showing exemplary results of an imaging analysis of sections of pancreas using the molecular probe for imaging according to Example 3.

Figure 9:
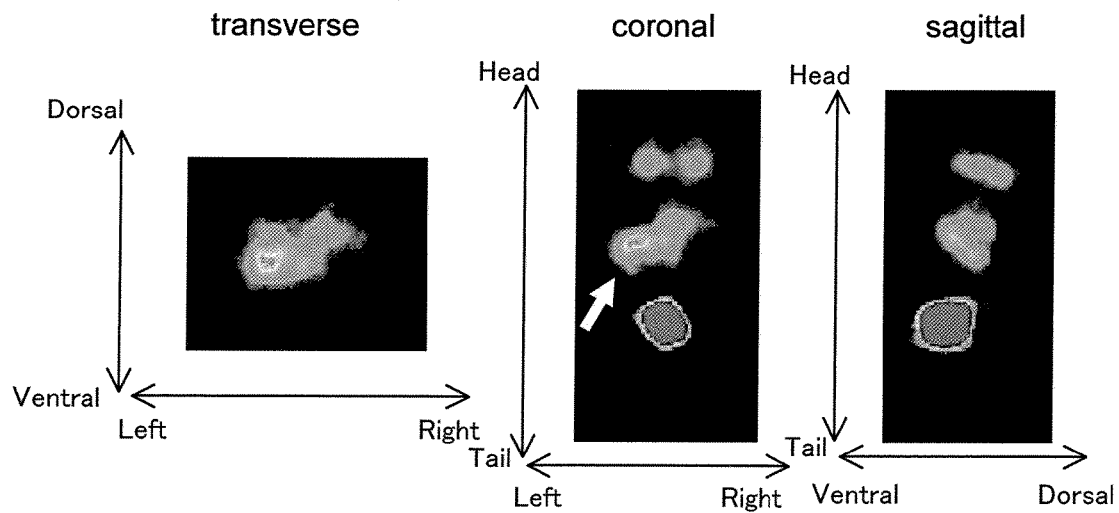

FIG. 9 shows images showing exemplary results of SPECT imaging using a molecular probe for imaging according to Example 4.

Figure 10:
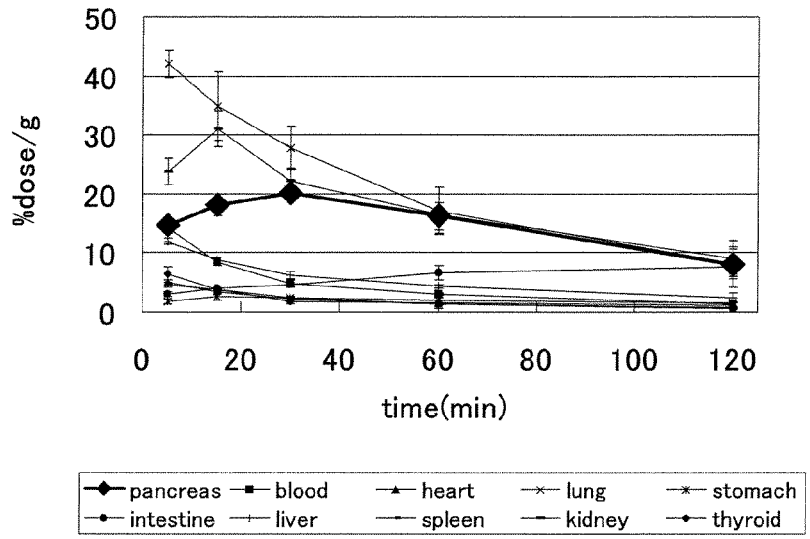

FIG. 10 is a graph showing exemplary variations with time in biodistribution of the molecular probe for imaging according to Example 5.

Figure 11:
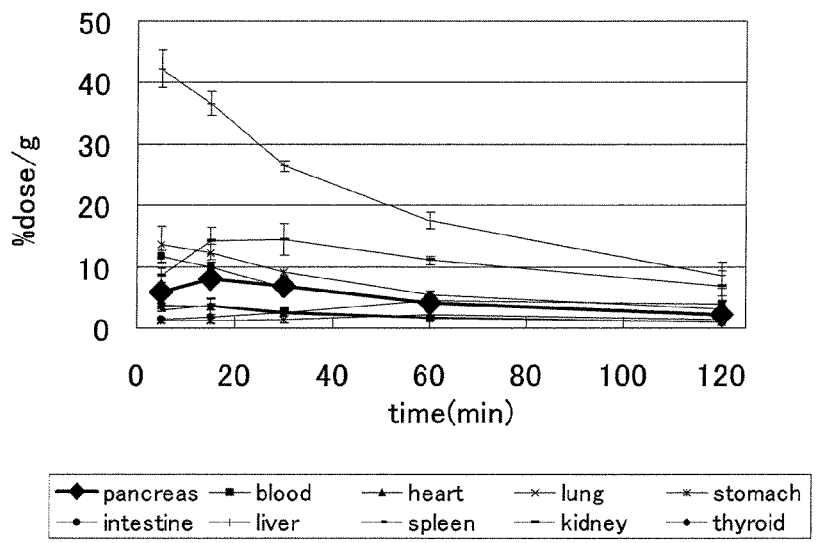

FIG. 11 is a graph showing exemplary variations with time in biodistribution of the molecular probe of Reference Example 4.

Figure 12:
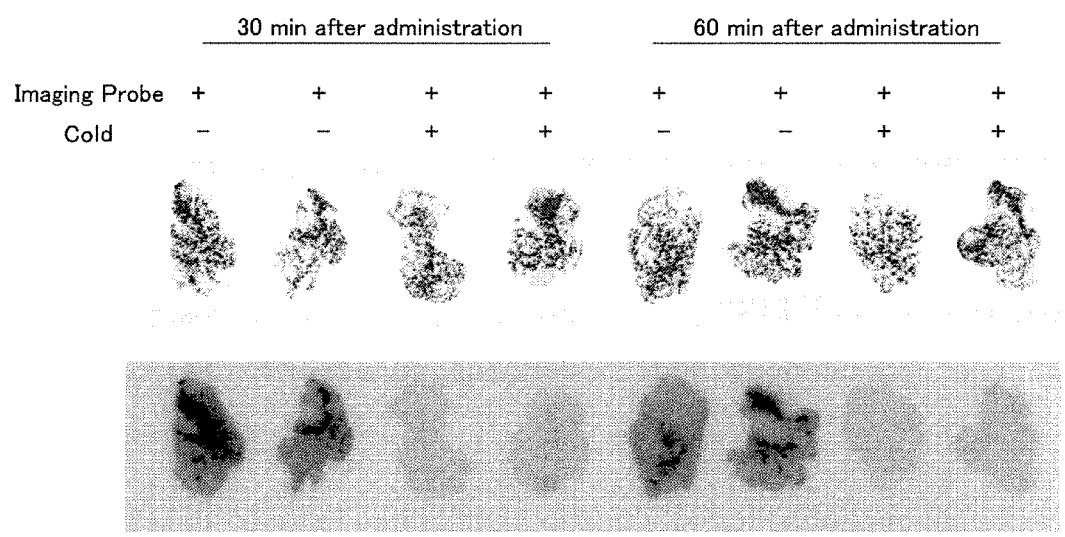

FIG. 12 shows images showing exemplary results of imaging analysis of pancreas sections using the molecular probe for imaging according to Example 5.

DESCRIPTION OF THE PREFERRED EMBODIMENTS

The diameter of a pancreatic islet is, for example, approximately 50 to 500 μm in the case of a human. In order to noninvasively image or quantify such pancreatic islets in vivo, a molecular probe, for example, is considered to be necessary that can accumulate specifically in pancreatic islets, thereby making contrast between pancreatic islets and surrounding organs. The aforementioned various researches and developments of molecular probes therefore have been made, but from the viewpoint of clearer imaging or more accurate quantification, a new molecular probe has been desired that accumulates more specifically in the pancreas and provides a desired contrast (S/N ratio) with respect to surrounding organs.

The present invention was made based on the finding that a molecular probe that comprises a polypeptide represented by the aforementioned formula (1), (2), or (3), or a polypeptide having homology with the aforementioned polypeptide, exhibits an improved uptake in the pancreas and an improved specificity with respect to the pancreas, and thus, it is possible to provide a molecular probe that is suitable for the noninvasive three-dimensional imaging of pancreatic islets by positron emission tomography (PET) or single photon emission computed tomography (SPECT).

Specifically, the present invention achieves an effect of providing, preferably, a molecular probe suitable for three-dimensional imaging of pancreatic islets by PET or SPECT, and more preferably, a molecular probe suitable for noninvasive three-dimensional imaging of pancreatic islets by PET. Further, the present invention achieves, for example, an effect of detecting an amount of pancreatic islets and/or an amount of pancreatic β-cells, and moreover, enabling the clarification of pathogenesis, the ultra-early diagnosis, and the prevention of development of type-II diabetics.

In other words, the present invention relates to the following:

[1] A molecular probe for use in imaging of pancreatic islets, the molecular probe comprising any one of the following polypeptides:

a polypeptide represented by the following formula (1), (2), or (3);

a polypeptide that is obtained by deletion, insertion, or substitution of one to several amino acids with respect to the polypeptide represented by the following formula (1), (2), or (3) and that is capable of binding to pancreatic islets; and a polypeptide that has a homology of 80% or higher with the amino acid sequence of the polypeptide represented by the following formula (1), (2), or (3) and that is capable of binding to pancreatic islets,

```
                                                    (SEQ ID NO. 1)
Z-HGEGTFTSDLSXQMEEEAVRLFIEWLKNGGPSSGAPPPS-NH2  (1)

(SEQ ID NO. 2)
Z-HGEGTFTSDLSKQMEEEAVRLFIEWLXNGGPSSGAPPPS-NH2  (2)

(SEQ ID NO. 3)
B-HGEGTFTSDLSKQMEEEAVRLFIEWLKNGGPSSGAPPPS-NH2  (3)
``` where the formulae (1) and (2),

"X" represents a lysine residue, an amino group of a side chain of the lysine residue being labeled with a radioactive nuclide, and "Z—" indicates that an α-amino group at an N-terminus is not modified, or is modified with a modifying group having no electric charge, in the formula (3), "B—" indicates that an α-amino group at an N-terminus is labeled with a radioactive nuclide, and in the formulae (1), (2), and (3), "—NH$_2$" indicates that a carboxyl group at a C-terminus is amidated.

[2] The molecular probe for imaging according to [1], wherein the radioactive nuclide is $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, or $^{186}$Re.

[3] The molecular probe for imaging according to [1] or [2], wherein the amino group of the side chain of the lysine labeled with the radioactive nuclide is bonded to a group represented by a chemical formula (I) shown below,

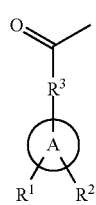

(I)

wherein

A represents an aromatic hydrocarbon group or an aromatic heterocyclic group,

R$^1$ represents a substituent that contains a radioactive nuclide,

R$^2$ represents either a hydrogen atom, or one or more substituents different from that represented by R$^1$, and R$^3$ represents any one of a bond, an alkylene group having 1 to 6 carbon atoms, and an oxyalkylene group having 1 to 6 carbon atoms.

[4] A precursor of a molecular probe for imaging, the precursor being used for producing the molecular probe for imaging according to any one of [1] to [3], the precursor comprising any one of the following polypeptides:

a polypeptide represented by the following formula (4), (5), or (6):

a polypeptide that is obtained by deletion, insertion, or substitution of one to several amino acids with respect to the polypeptide represented by the following formula (4), (5), or (6) and that is capable of binding to pancreatic islets after being labeled and deprotected; and a polypeptide that has a homology of 80% or higher with the amino acid sequence of polypeptide represented by the following formula (4), (5), or (6) and that is capable of binding to pancreatic islets after being labeled and deprotected:

```
                                                    (SEQ ID NO. 4)
*-HGEGTFTSDLSKQMEEEAVRLFIEWLK*NGGPSSGAPPPS-NH2  (4)

(SEQ ID NO. 5)
*-HGEGTFTSDLSK*QMEEEAVRLFIEWLKNGGPSSGAPPPS-NH2  (5)

(SEQ ID NO. 6)
HGEGTFTSDLSK*QMEEEAVRLFIEWLK*NGGPSSGAPPPS-NH2   (6)
``` where in the formulae (4) and (5),

"*-" indicates that an α-amino group at an N-terminus is protected by a protecting group, or is modified with a modifying group having no electric charge, in the formulae (4), (5), and (6), "K*" indicates that an amino group of a side chain of a lysine is protected by a protecting group, and "—NH$_2$" indicates that a carboxyl group at a C-terminus is amidated.

[5] A method for producing the molecular probe for imaging according to any one of [1] to [3], the method comprising:
labeling and deprotecting the precursor of a molecular probe for imaging according to [4].

[6] The method according to [5] for producing the molecular probe for imaging, wherein the labeling of the precursor of a molecular probe for imaging includes labeling the precursor, using a compound containing a radioactive nuclide of $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, or $^{186}$Re.

[7] The method according to [5] or [6] for producing the molecular probe for imaging, wherein the labeling of the precursor of a molecular probe for imaging includes labeling of the precursor, using a compound having a group represented by the following chemical formula (I),

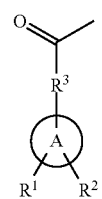

(I)

wherein

A represents an aromatic hydrocarbon group or an aromatic heterocyclic group,

R$^1$ represents a substituent that contains a radioactive nuclide,

R² represents either a hydrogen atom, or one or more substituents different from that represented by R¹, and R³ represents any one of a bond, an alkylene group having 1 to 6 carbon atoms, and an oxyalkylene group having 1 to 6 carbon atoms.

[8] A kit for imaging of pancreatic islets, the kit comprising at least one of the molecular probe for imaging according to any one of [1] to [3] and the precursor of a molecular probe for imaging according to [4].

[9] The kit according to [8], wherein the molecular probe for imaging included in the kit is in a form of a parenteral solution.

[10] A reagent for imaging of pancreatic islets, the reagent comprising the molecular probe for imaging according to any one of [1] to [3].

[11] A method for imaging of pancreatic islets, the method comprising detecting a signal of the molecular probe for imaging according to any one of [1] to [3] from an analyte to which the molecular probe has been administered.

[12] The method for imaging according to [11], further comprising reconfiguring the detected signal to convert the signal into an image, and displaying the image.

[13] The method for imaging according to [11] or [12], the method further comprising determining a state of pancreatic islets on the basis of results of the imaging of pancreatic islets using the molecular probe for imaging.

[14] A method for determining an amount of pancreatic islets, the method comprising:

detecting a signal of the molecular probe for imaging according to any one of [3] from an analyte to which the molecular probe has been administered; and calculating an amount of pancreatic islets from the detected signal of the molecular probe for imaging.

[15] The method for determining an amount of pancreatic islets according to [14], further comprising presenting the calculated amount of pancreatic islets.

In the present specification, the "imaging of pancreatic islets" refers to molecular imaging of pancreatic islets, and includes the imaging of in vivo spatial and/or time distribution of pancreatic islets. Further, in the present invention, the imaging of pancreatic islets preferably images pancreatic β-cells as target molecules, and more preferably GLP-1R of pancreatic β-cells as target molecules from the viewpoint of the prevention, treatment, and diagnosis of diabetes. Still further, in the present invention, the imaging of pancreatic islets preferably is noninvasive three-dimensional imaging, from the viewpoint of quantifiability of an amount of pancreatic islets and applicability to humans. The method for imaging is not limited particularly, if it is a method that enables noninvasive imaging of pancreatic islets, and various methods are usable such as positron emission tomography (PET) and single photon emission computed tomography (SPECT).

In the present specification, the description of "polypeptide capable of binding to pancreatic islets" means that a polypeptide is capable of binding to cells that compose pancreatic islets, preferably capable of binding to pancreatic β-cells, more preferably capable of specifically binding to pancreatic β-cells, and still more preferably capable of specifically binding to GLP-1R of pancreatic β-cells. Further, "capable of specifically binding to . . . " means as follows: in the noninvasive imaging using the molecular probe for imaging according to the present invention, the probe preferably has a specificity such that a signal therefrom can be detected with a contrast sufficiently distinguishable from surrounding organs such as other organs, and more preferably has a specificity such that a desired contrast (S/N ratio) with respect to surrounding organs can be obtained.

[Molecular Probe for Imaging of the Present Invention]

The molecular probe for imaging of the present invention is a molecular probe used in imaging of pancreatic islets that comprises any one of the following polypeptides: a polypeptide represented by the aforementioned formula (1), (2), (3); a polypeptide that is obtained by deletion, insertion, or substitution of one to several amino acids with respect to the polypeptide of the foregoing formula (1), (2), or (3), and that is capable of binding to pancreatic islets; and a polypeptide that has a homology of 80% or higher with the amino acid sequence of the polypeptide of the foregoing formula (1), (2), or (3), and that is capable of binding to pancreatic islets. The molecular probe for imaging of the present invention preferably is a molecular probe for imaging of pancreatic islets that consists of any one of the following polypeptides: a polypeptide represented by the aforementioned formula (1), (2), or (3); a polypeptide that is obtained by deletion, insertion, or substitution of one to several amino acids with respect to the polypeptide of the foregoing formula (1), (2), or (3), and that is capable of binding to pancreatic islets; and a polypeptide that has a homology of 80% or higher with the amino acid sequence of the polypeptide of the foregoing formula (1), (2), or (3), and that is capable of binding to pancreatic islets.

The molecular probe for imaging of the present invention can be used in, for example, three-dimensional imaging of pancreatic islets, preferably noninvasive three-dimensional imaging of pancreatic islets, and more preferably quantification of an amount of pancreatic islets.

The amino acid sequence of the polypeptide of the formula (1) is an amino acid sequence according to SEQ ID NO. 1 shown in the Sequence Listing. An amino group of a side chain of a lysine at position 12 in the polypeptide of the formula (1) above is labeled with a radioactive nuclide. An amino acid sequence of the polypeptide of the formula (2) above is an amino acid sequence according to SEQ ID NO. 2 in the Sequence Listing, and an amino group of a side chain of a lysine at position 27 in the polypeptide of the formula (2) above is labeled with a radioactive nuclide. Each of α-amino groups at N-terminus of the polypeptides of the formulae (1) and (2) is either not modified, or modified with a modifying group having no electric charge. Each of carboxyl groups at C-terminus of the polypeptides of the formulae (1) and (2) is amidated with an amino group from the viewpoint of improving the affinity to the pancreatic β-cells and/or the stability in vivo.

The amino acid sequence of the polypeptide of the formula (3) above is an amino acid sequence according to SEQ ID NO. 3 in the Sequence Listing, and an α-amino group at an N-terminus of the polypeptide of the formula (3) above is labeled with a radioactive nuclide. Further, a carboxyl group at a C-terminus of the polypeptide of the formula (3) above is amidated with an amino group from the viewpoint of improving the affinity to the pancreatic β-cells and/or the stability in vivo.

Here, the sequence of the amino acids in the foregoing formula (1) (SEQ ID NO. 1 in the Sequence Listing) and the sequence of the amino acids in the foregoing formula (2) (SEQ ID NO. 2 in the Sequence Listing) are identical to the amino acid sequence of exendin-4 except for a lysine residue labeled with a radioactive nuclide.

Further, the sequence of the amino acids in the foregoing formula (3) (SEQ ID NO. 3 in the Sequence Listing) is identical to the amino acid sequence of exendin-4 except for an α-amino group at an N-terminus labeled with a radioactive nuclide. It is known that exendin-4 is an analog of GLP-1, and bonds to GLP-1R expressed on the pancreatic β-cell, thereby functioning as an agonist. The molecular probe for imaging of the present invention also is capable of binding to pancreatic islets, preferably capable of binding to the pancreatic β-cells, and more preferably capable of binding to GLP-1R of the pancreatic β-cells.

Further, in another embodiment of the present invention, the molecular probe for imaging of the present invention may include a polypeptide used in imaging that is obtained by deletion, insertion, or substitution of one to several amino acids with respect to the polypeptide of the foregoing formula (1), (2), or (3), and that is capable of binding to pancreatic islets. Here, exemplary ranges expressed by the foregoing description of "one to several" include the following ranges: 1 to 10; 1 to 9; 1 to 8; 1 to 7; 1 to 6; 1 to 5; 1 to 4; 1 to 3; 1 to 2; and 1. In the molecular probe for imaging according to this embodiment of the present invention also, in the case of the polypeptide obtained by deletion, insertion, or substitution of one to several amino acids with respect to the polypeptide of the foregoing formula (1) or (2), it is preferable that the polypeptide includes one lysine labeled with a radioactive nuclide, and that a carboxyl group at a C-terminus is amidated. Further, an α-amino group at an N-terminus may not be modified, or may be modified with a modifying group having no electric charge. In the molecular probe for imaging according to this embodiment of the present invention, in the case where it is the polypeptide obtained by deletion, insertion, or substitution of one to several amino acids with respect to the polypeptide of the foregoing formula (3), it is preferable that an α-amino group at an N-terminus is labeled with a radioactive nuclide, and that a carboxyl group at a C-terminus is amidated. The polypeptide obtained by deletion, insertion, or substitution of one to several amino acids with respect to the polypeptide of the foregoing formula (1), (2), or (3) preferably has the same working effect as that of the polypeptide of the foregoing formula (1), (2), or (3), and more preferably has the same working effect as that of the polypeptide of the formula (1).

In still another embodiment of the present invention, the molecular probe for imaging of the present invention may include a polypeptide used in imaging that has a homology of 80% or higher with the amino acid sequence of the polypeptide of the foregoing formula (1), (2), or (3), and that is capable of binding to pancreatic islets. Here, the "homology" may be any value calculated by an algorithm usually used by those skilled in the art, for example, BLAST or FASTA, or alternatively, it may be based on a value obtained by dividing the number of identical amino acid residues existing in two polypeptides compared, by the number of amino acids of an entire length of one of the polypeptides. Exemplary ranges of the homology may include the following ranges: not less than 85%; not less than 90%; and not less than 95%. In the molecular probe for imaging according to this embodiment of the present invention also, in the case of a polypeptide having a homology of 80% or higher with the polypeptide of the foregoing formula (1) or (2), it is preferable that the polypeptide includes one lysine labeled with a radioactive nuclide, that a carboxyl group at a C-terminus is amidated, and that an α-amino group at an N-terminus may not be modified, or may be modified with a modifying group having no electric charge. In the molecular probe for imaging of this embodiment of the present invention also, in the case of a polypeptide having a homology of 80% or higher with the polypeptide of the foregoing formula (3), it is preferable that an α-amino group at an N-terminus is labeled with a radioactive nuclide, and that a carboxyl group at a C-terminus is amidated. The polypeptide having a homology of 80% or higher with the amino acid sequence of the polypeptide of the foregoing formula (1), (2), or (3) preferably has a working effect identical to that of the polypeptide of the formula (1), (2), or (3), and more preferably has a working effect identical to that of the polypeptide of the foregoing formula (1).

[Amino Group Labeled with Radioactive Nuclide]

The amino group of the side chain of the lysine residue represented by X in the amino acid sequence of the polypeptide of the aforementioned formula (1) or (2), that is, the amino group of the side chain of the lysine at position 12 in the polypeptide of the aforementioned formula (1) and the amino group of the side chain of the lysine at position 27 in the polypeptide of the aforementioned formula (2) are labeled with radioactive nuclides. Besides, the α-amino group at the N-terminus of the polypeptide of the aforementioned formula (3) is labeled with a radioactive nuclide.

Examples of the radioactive nuclide include $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{82}$Rb, $^{99m}$Tc, $^{111}$In, $^{123}$I, $^{124}$I, $^{125}$I, $^{131}$I, and $^{186}$Re. From the viewpoint of performing PET, the radioactive nuclide preferably is a positron emission nuclide such as $^{11}$C, $^{13}$N, $^{15}$O, $^{18}$F, $^{62}$Cu, $^{64}$Cu, $^{68}$Ga, $^{75}$Br, $^{76}$Br, $^{82}$Rb, or $^{124}$I, From the viewpoint of performing SPECT, the radioactive nuclide preferably is a γ-emission nuclide such as $^{67}$Ga, $^{99m}$Tc, $^{77}$Br, $^{111}$In, $^{123}$I, or $^{125}$I. Among these, radioactive halogen nuclides such as $^{18}$F, $^{75}$Br, $^{76}$Br, $^{77}$Br, $^{123}$I, and $^{124}$I are preferred more, and $^{18}$F, $^{123}$I, and $^{124}$I are preferred particularly.

Each of an amino group of a side chain of a lysine labeled with a radioactive nuclide and an α-amino group at an N-terminus labeled with a radioactive nuclide preferably is bonded to a group represented by the chemical formula (I) shown below. A radioactive nuclide is bonded to a lysine with use of the group represented by the chemical formula (I) below, whereby the molecular probe for imaging according to the present invention can be caused to accumulate more specifically in the pancreatic islets, and preferably the molecular probe for imaging according to the present invention can be caused to accumulate more specifically in GLP-1R of pancreatic β-cells:

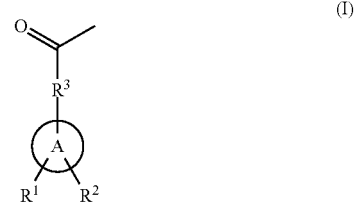

In the foregoing chemical formula (I), A represents an aromatic hydrocarbon group or an aromatic heterocyclic group. The aromatic hydrocarbon group preferably is an aromatic hydrocarbon group having 6 to 18 carbon atoms, and examples of the same include phenyl group, o-tolyl group, m-tolyl group, p-tolyl group, 2,4-xylyl group, p-cumenyl group, mesityl group, 1-naphthyl group. 2-naphthyl up, 1-anthryl group, 2-anthryl group, 9-anthryl group, 1-phenanthryl group, 9-phenanthryl group, 1-acenaphthyl group, 2-azulenyl group, 1-pyrenyl group, 2-triphenylenyl group, o-biphenylyl group, m-biphenylyl group, p-biphenylyl group, and terphenyl group. The aromatic heterocyclic group preferably is a 5 to 10-membered heterocyclic group having one or two of a nitrogen atom, an oxygen atom, or a sulfur atom, and examples of the same include triazolyl group, 3-oxadiazolyl group, 2-furyl group, 3-furyl group, 2-thienyl group, 3-thienyl group, 1-pyrrolyl group, 2-pyrrolyl group, 3-pyrrolyl group, 2-pyridyl group, 3-pyridyl group, 4-pyridyl group, 2-pyradyl group, 2-oxazolyl group, 3-isoxyazolyl group, 2-thiazolyl group, 3-isothiazolyl group, 2-imidazolyl group, 3-pyrazolyl group, 2-quinolyl group, 3-quinolyl group, 4-quinolyl group, 5-quinolyl group, 6-quinolyl group, 7-quinolyl group, 8-quinolyl group, 1-isoquinolyl group, 2-quinoxalynyl group, 2-benzofuryl group, 2-benzothienyl group, N-indolyl group, and N-carbazolyl group. A preferably is, among these, phenyl group, triazolyl group, or pyridyl group, and more preferably, phenyl group.

In the aforementioned chemical formula (I), $R^1$ represents a substituent that contains a radioactive nuclide. Examples of the "substituent that contains a radioactive nuclide" in the present specification include the aforementioned radioactive nuclides; radioactive-nuclide-substituted $C_1$-$C_3$ alkyl groups in which a hydrogen atom is substituted with the aforementioned radioactive nuclide; and radioactive-nuclide-substituted $C_1$-$C_3$ alkoxy groups in which a hydrogen atom is substituted with the aforementioned radioactive nuclide. In the present specification, the "$C_1$-$C_3$ alkyl group" refers to an alkyl group that has 1 to 3 carbon atoms, and examples of the same include methyl group, ethyl group, and propyl group. In the present specification, the "radioactive-nuclide-substituted $C_1$-$C_3$ alkyl group" refers to an alkyl group that has 1 to 3 carbon atoms and in which a hydrogen atom is substituted with the aforementioned radioactive nuclide. In the present specification, the "$C_1$-$C_3$ alkoxy group" refers to an alkoxy group that has 1 to 3 carbon atoms, and examples of the same include methoxy group, ethoxy group, and propoxy group. In the present specification, the "radioactive-nuclide-substituted. $C_1$-$C_3$ alkoxy group" refers to an alkoxy group that has 1 to 3 carbon atoms and in which a hydrogen atom is substituted with the aforementioned radioactive nuclide. Among these, $R^1$ preferably is a substituent containing a radioactive halogen, that is, for example, a substituent containing $^{18}F$, $^{75}Br$, $^{76}Br$, $^{77}Br$, $^{123}I$, $^{124}I$, $^{125}I$, or $^{131}I$. From the viewpoint of performing PET, $R^1$ preferably is a substituent containing a radioactive nuclide that emits positron, that is, for example, a substituent containing $^{18}F$, $^{75}Br$, $^{76}Br$, or $^{124}I$. From the viewpoint of performing SPECT, $R^1$ preferably is a substituent containing a radioactive nuclide that emits γ-rays, that is, for example, a substituent containing $^{77}Br$, $^{99m}Tc$, $^{111}In$, $^{123}I$, or $^{125}I$. In $R^1$, preferably a hydrogen atom at any one of an ortho-position, a meta-position, and a para-position is substituted with a radioactive nuclide, from the viewpoint of quantification, and more preferably, at a meta-position or a para-position.

In the aforementioned chemical formula (I), $R^2$ represents a hydrogen atom or one or more substituents different from that represented by $R^1$. $R^2$ may be a hydrogen atom or a substituent, but preferably, it is a hydrogen atom. In other words, in the aforementioned chemical formula (I), A preferably does not have a substituent other than $R^1$. In the case where $R^2$ represents a plurality of substituents, these substituents may be identical or different. Examples of the substituent include hydroxyl group, electron attractive groups, electron donative groups, $C_1$-$C_6$ alkyl groups, $C_2$-$C_6$ alkenyl groups, and $C_2$-$C_6$ alkynyl groups. Examples of the electron attractive group include cyano group, nitro group, halogen atoms, carbonyl group, sulfonyl group, acetyl group, sulfonyl group, and phenyl group. Examples of the halogen atom include fluorine atom, chlorine atom, bromine atom, and iodine atom. In the present specification, the "$C_1$-$C_6$ alkyl group" refers to an alkyl group having 1 to 6 carbon atoms, and examples of the same include methyl group, ethyl group, propyl group, isopropyl group, butyl group, isobutyl group, sec-butyl group, tert-butyl group, pentyl group, isopentyl group, and hexyl group. In the present specification, the "$C_2$-$C_6$ alkenyl group" refers to an alkenyl group having 2 to 6 carbon atoms, and examples of the same include vinyl group, 1-propenyl group, 2-propenyl group, isopropenyl group, 1-butenyl group, 2-butenyl group, and 3-butenyl group. In the present specification, the "$C_2$-$C_6$ alkynyl group" refers to an alkynyl group having 2 to 6 carbon atoms, and examples of the same include ethynyl group, 1-propynyl group, 2-propynyl group, 1-butynyl group, 2-butynyl group, and 3-butynyl group. Among these, the substituent preferably is a hydroxyl group or an electron attractive group.

In the aforementioned chemical formula (I), $R^3$ preferably is a bond, a $C_1$-$C_6$ alkenyl group, or a $C_1$-$C_6$ oxyalkylene group. In the present specification, the "$C_1$-$C_6$ alkenyl group" refers to an alkylene group having 1 to 6 carbon atoms, and examples of the same include straight-chain or branched-chain alkylene groups such as methylene group, ethylene group, propylene group, butylene group, pentyl group, and hexyl group. In the present specification, the "$C_1$-$C_6$ oxyalkylene group" refers to an oxyalkylene group having 1 to 6 carbon atoms, and examples of the same include oxymethylene group, oxyethylene group, oxypropylene group, oxybutylene group, and oxypentyl group. $R^3$ preferably is a bond, methylene group, or ethylene group, and more preferably, a bond, from the viewpoint of the affinity between the molecular probe and pancreatic islets, preferably the affinity between the molecular probe and pancreatic β-cells, and more preferably the affinity between the molecular probe and GLP-1R of pancreatic β-cells.

In the group represented by the chemical formula (I) above, from the viewpoint of the affinity between the molecular probe for imaging of the present invention and pancreatic islets, preferably the affinity between the molecular probe and pancreatic β-cells, and more preferably the affinity between the molecular probe and GLP-1R of pancreatic β-cells, it is preferable that A represents a phenyl group, $R^2$ represents a hydrogen atom, and $R^3$ represents a bond, and it is more preferable that A represents a phenyl group, $R^1$ represents a [$^{18}F$]fluorine atom or [$^{123/124/125/131}I$]iodine atom, $R^2$ represents a hydrogen atom, and $R^3$ represents a bond. In other words, the group represented by the aforementioned chemical formula (I) preferably is a group represented by the following chemical formula (Ia), and more preferably a group represented by the following chemical formula (Ib) ([$^{18}F$]fluorobenzoyl group), a group represented by the following chemical formula (Ic) ([$^{123}I$]3-iodobenzoyl group), a group represented by the following chemical formula (Id) ([$^{124}I$]3-iodobenzoyl group), a group represented by the following chemical formula (Ie) ([$^{125}I$]3-iodobenzoyl group), or a group represented by the following chemical formula (If) ([$^{131}I$]3-iodobenzoyl group). In the chemical formula (Ia), $R^1$ is as described above.

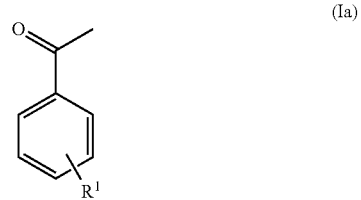

(Ia)

-continued

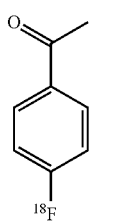

(Ib)

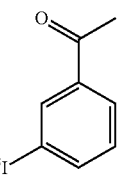

(Ic)

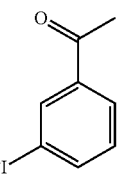

(Id)

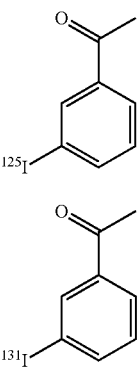

(Ie)

(If)

Further, the amino group of the side chain of the lysine labeled with the radioactive nuclide may be labeled with a metal nuclide via a chelating site that can be chelating a metal radioactive isotope (metal nuclide). Examples of the metal nuclide include $^{64}$Cu, $^{67}$Ga, $^{68}$Ga, $^{82}$Rb, $^{99m}$Tc, $^{111}$In, and $^{186}$Re. Examples of the compound that can form a chelating site include diethylenetriaminepentaacetic acid (DTPA), 6-hydrazinopyridine-3-carboxylic acid (HYNIC), tetraazacyclododecanetetraacetic acid (ROTA), dithisosemicarbazone (DTS), diaminedithiol (DART), mercaptoacetylglycylglycylglycine (MAG3), monoamidemonoarninedithiol (MAMA), diamideclithiol (DADS), and propylene diamine dioxime (PnAO).

[Modifying Group]

In the molecular probe for imaging of the present invention, an α-amino group at an N-terminus in the polypeptide of the above-described formula (1) or (2) may be modified with a modifying group having no electric charge, from the viewpoint of canceling a positive charge of the α-amino group at the N-terminus thereby suppressing accumulation in kidneys of the molecular probe for imaging of the present invention. Examples of such a modifying group having no electric charge include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), and allyloxycarbonyl group (Alloc), 4-methoxytrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethyl-benzenesulfonyl group (Mtr), mesitylene-2-sulfonyl group (Mts), 4,4-dimethoxybenzohydryl group (Mbh), tosyl group (Tbs), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene) ethyl group (Dde), 2,6-dichlorobenzyl group (2,6-DiCl—Bzl), 2-chlorobenzyloxycarbonyl group (2-Cl—Z), 2-bromobenzyloxycarbonyl group (2-Br—Z), benzyloxymethyl group (Bom), velohexyloxy group (cHxO), t-butoxymethyl group (Bum), t-butoxy group (tBuO), t-butyl group (tBu), acetyl group (Ac), trifluoroacetyl group (TFA), o-bromobenzyloxycarbonyl group, t-butyldimethylsilyl group, 2-chlorobenzyl (Cl-z) group, cyclohexyl group, cyclopentyl group, isopropyl group, pivalyl group, tetrahydropyran-2-yl group, and trimethylsilyl group. Among these, preferably, the modifying group is acetyl group, benzyl group, benzyloxymethyl group, o-bromobenzyloxycarbonyl group, t-butyl group, t-butyklimethylsilyl group, 2-chlorobenzyl group, 2,6-dichlorobenzyl group, cyclohexyl group, cyclopentyl group, isopropyl group, pivalyl group, tetrahydropyran-2-yl group, tosyl group, trimethylsilyl group, or trityl group. More preferably, the modifying group is acetyl group.

In still another embodiment of the present invention, the molecular probe for imaging of the present invention includes a polypeptide that is obtained by deletion of 1, 2, 3, 4, 5, 6, or 7 amino acids on the N-terminus side in the polypeptide represented by the formula (1) above (SEQ ID NO. 1) or the polypeptide represented by the formula (2) above (SEQ ID NO. 2) and that is capable of binding to pancreatic islets, or a polypeptide that has homology with this polypeptide and that is capable of bonding to pancreatic islets; and preferably, it is a molecular probe for imaging of pancreatic islets that consists of the aforementioned polypeptide. As for the molecular probe for imaging according to the present embodiment, in a polypeptide having homology with the polypeptide of the formula (1), an amino group of a side chain of a lysine corresponding to the lysine at position 12 in the polypeptide of the formula (1) above is labeled with a radioactive nuclide. Further, in a polypeptide having homology with the polypeptide of the formula (2), an amino group of a side chain of a lysine corresponding to a lysine at position 27 in the polypeptide of the formula (2) is labeled with a radioactive nuclide. It is preferable that an α-amino group at an N-terminus of the polypeptide is either not modified or modified with a modifying group having no electric charge, and that a carboxyl group at a C-terminus is amidated. Examples of polypeptide having homology with the aforementioned polypeptide include the following polypeptides: a polypeptide that is obtained by deletion, insertion, or substitution of one to several amino acids with respect to the polypeptide represented by the formula (1) above (SEQ ID NO. 1) or the polypeptide represented by the formula (2) above (SEQ ID NO. 2) from which 1, 2, 3, 4, 5, 6, or 7 amino acids on the N-terminus side are deleted; and a polypeptide that has homology of 80% or higher with the amino acid sequence of the foregoing polypeptide.

In another embodiment of the present invention, the molecular probe for imaging according to the present invention includes a polypeptide represented by the formula (3) above (SEQ ID NO. 3) from which 1, 2, 3, 4, 5, 6, or 7 amino acids on the N-terminus side are deleted and that is capable of binding to pancreatic islets, or a polypeptide that has homology with this polypeptide and that is capable of bonding to pancreatic islets; and preferably, it is a molecular probe for imaging of pancreatic islets that consists of the aforementioned polypeptide. In the molecular probe for imaging according to the present embodiment, an α-amino group at an N-terminus of the polypeptide is labeled with a radioactive nuclide. Besides, a carboxyl group at a C-terminus preferably is amidated. Examples of the polypeptide represented by the formula (3) above (SEQ ID NO. 3) from which 1, 2, 3, 4, 5, 6, or 7 amino acids on the N-terminus side are deleted include the following polypeptides: a polypeptide that is obtained by deletion, insertion, or substitution of one to several amino acids with respect to the polypeptide that is obtained by deletion of 1, 2, 3, 4, 5, 6, or 7 amino acids on the N-terminus side in the polypeptide represented by the formula (3) above (SEQ ID NO. 3); and a polypeptide that has homology of 80% or higher with the amino acid sequence of the foregoing polypeptide.

In still another embodiment of the present invention, the molecular probe for imaging of the present invention includes a polypeptide obtained by deletion of 1 to 9, 1 to 8, 1 to 7, 1 to 6, 1 to 5, 1 to 4, 1 to 3, 1 to 2, or 1 amino acid from the C-terminus side of the polypeptide of the formula (1), (2) or (3) and capable of binding to pancreatic islets, or a polypeptide having homology with this polypeptide and capable of binding to pancreatic islets; and preferably, it is a molecular probe for imaging of pancreatic islets that consists of the aforementioned polypeptide. As for the molecular probe for imaging according to the present embodiment, the carboxyl group at the C-terminus is preferably amidated and the α-amino group at the N-terminus may be unmodified or modified with a modifying group having no electric charge.

As described above, the molecular probe for imaging according to the present invention can be used in, for example, imaging of pancreatic islets, preferably imaging of pancreatic β-cells, and more preferably imaging of GL-1R of pancreatic β-cells. From the viewpoint of uses for examination and diagnosis of humans, the molecular probe for imaging according to the present invention is preferably used in noninvasive imaging of pancreatic islets, and is also preferably used in imaging of pancreatic islets for quantifying an amount of the pancreatic islets, from the same viewpoint. Moreover, the molecular probe for imaging according to the present invention can also be used in imaging for prevention, treatment, or diagnosis of diabetes. Further, the molecular probe for imaging according to the present invention can be used as, for example, a composition, an imaging reagent, a contrast medium or a diagnostic imaging agent containing the molecular probe for imaging according to the present invention as an effective ingredient and used in imaging as described above. The composition, the diagnostic imaging agent and the like can be in the form of solution or powder, for example. However, in consideration of the half-life of a radioactive nuclide and radioactive decay, they are preferably in the form of parenteral solution.

[Precursor of Molecular Probe for Imaging of the Present Invention]

Another aspect of the present invention relates to a precursor of a molecular probe (hereinafter referred to as molecular probe precursor) for imaging, for use in production of the molecular probe for imaging of the present invention, wherein the precursor contains any one of the following polypeptides: a polypeptide represented by the following formula (4), (5), or (6); a polypeptide that is obtained by deletion, insertion, or substitution of one to several amino acids with respect to the polypeptide of the following formula (4), (5), or (6) and that is capable of binding to pancreatic islets after being labeled and deprotected; and a polypeptide that has a homology of 80% or higher with the amino acid sequence of polypeptide of the following formula (4), (5), or (6) and that is capable of binding to pancreatic islets after being labeled and deprotected. The molecular probe for imaging of the present invention can be prepared using, for example, the precursor of the molecular probe for imaging of the present invention.

```
                                                  (SEQ ID NO. 4)
*-HGEGTFTSDLSKQMEEEAVRLFIEWLK*NGGPSSGAPPPS-NH2  (4)

(SEQ ID NO. 5)
*-HGEGTFTSDLSK*QMEEEAVRLFIEWLKNGGPSSGAPPPS-NH2  (5)

(SEQ ID NO. 6)
 HGEGTFTSDLSK*QMEEEAVRLFIEWLK*NGGPSSGAPPPS-NH2  (6)
``` where in the formulae (4) and (5),

"*-" indicates that an α-amino up at an N-terminus is protected by a protecting group, or is modified with a modifying group having no electric charge, and in the formulae (4), (5), and (6), "K*" indicates that an amino group of a side chain of a lysine is protected by a protecting group, and "—NH$_2$" indicates that a carboxyl group at a C-terminus is amidated.

The molecular probe precursor of the present invention preferably is a molecular probe precursor for imaging that consists of any one of the following polypeptides: a polypeptide of the foregoing formula (4), (5), or (6); a polypeptide that is obtained by deletion, insertion, or substitution of one to several amino acids with respect to the polypeptide of the foregoing formula (4), (5), or (6) and that is capable of binding to pancreatic islets after being labeled and deprotected; and a polypeptide that has a homology of 80% or higher with the amino acid sequence of the polypeptide of the foregoing formula (4), (5), or (6) and that is capable of binding to pancreatic islets after being labeled and deprotected.

The amino acid sequence of the polypeptide of the aforementioned formula (4) is the amino acid sequence according to SEQ ID NO. 4 shown in the Sequence Listing. A protecting group for protecting an amino group is bonded to an amino group of a side chain of a lysine at position 27 in the polypeptide of the formula (4), and a protecting group for protecting an amino group or a modifying group for modifying an amino group is bonded to an α-amino group at an N-terminus of the polypeptide of the formula (4). The amino acid sequence of the polypeptide of the aforementioned formula (5) is the amino acid sequence according to SEQ ID NO. 5 shown in the Sequence Listing. A protecting group for protecting an amino group is bonded to an amino group of a side chain of a lysine at position 12 in the polypeptide of the formula (5), and a protecting group for protecting an amino group or a modifying group for modifying an amino group is bonded to an α-amino group at an N-terminus of the polypeptide of the formula (5). When the molecular probe precursor of the present invention including the polypeptide of the aforementioned formula (4) or the polypeptide of the aforementioned formula (5) is labeled by a labeling system for labeling an amino group that will be described later, an amino group of a side chain of a lysine not protected by a protecting group can be labeled. In other words, in the polypeptide of the formula (4), the amino group of the side chain of a lysine at position 12 is labeled, and in the polypeptide of the formula (5), the amino group of the side chain of a lysine at position 27 is labeled. It should be noted that the α-amino group at the N-terminus of the polypeptide of the formula (4) or (5) is protected by a protecting group bonded thereto, or is modified with a modifying group having no electric charge.

The amino acid sequence of the polypeptide of the aforementioned formula (6) is an amino acid sequence according to SEQ ID NO. 6 in the Sequence Listing, and a protecting group for protecting an amino group is bonded to each of an amino group of a side chain of a lysine at position 12 and an amino group of a side chain of a lysine at position 27 in the polypeptide of the formula (6). When the molecular probe precursor of the present invention including the polypeptide of the above-described formula (6) is labeled by a labeling system for labeling an amino group that will be described later, the α-amino group at the N-terminus that is not protected by a protecting group can be labeled.

A carboxyl group at a C-terminus of each of the polypeptides of the formulae (4), (5), and (6) is amidated with an amino group from the viewpoint of improving the property of binding to pancreatic β-cells and/or the stability in vivo. It should be noted that in the molecular probe precursor of the present invention, a protecting group or an additional modifying group may or may not be, preferably may not be, bonded to the amidated carboxyl group at the C-terminus of each of the polypeptides of the formulae (4), (5), and (6). However, the scope of the present invention does not exclude an embodiment in which the amidated carboxyl group is protected by a protecting group or an embodiment in which a modifying group is bonded to the amidated carboxyl group.

Here, the sequence of the amino acids in each of the foregoing formula (4) (SEQ ID NO. 4 in the Sequence Listing) and the foregoing formula (5) (SEQ ID NO. 5 in the Sequence Listing) is identical to the amino acid sequence of exendin-4 except for a protecting group bonded to an amino group of a side chain of a lysine. Further, the sequence of the amino acids in the foregoing formula (6) (SEQ ID NO. 6 in the Sequence Listing) is identical to the amino acid sequence of exendin-4 except for a protecting group bonded to an amino group of a side chain of a lysine.

[Protecting Group]

The protecting group is intended to protect the other amino group of the molecular probe precursor than an amino group of a side chain of a desired lysine or an α-amino group at an N-terminus while the amino group of the side chain of a lysine or the α-amino group at the N-terminus is being labeled. As the protecting group, any known protecting group that can perform such a function can be used. The protecting group is not limited particularly, and examples of the same include 9-fluorenylmethyloxycarbonyl group (Fmoc), tert-butoxycarbonyl group (Boc), benzyloxycarbonyl group (Cbz), 2,2,2-trichloroethoxycarbonyl group (Troc), and allyloxycarbonyl group (Alloc), 4-methoxytrityl group (Mmt), amino group, alkyl groups having 3 to 20 carbon atoms, 9-fluoreneacetyl group, 1-fluorenecarboxylic acid group, 9-fluorenecarboxylic acid group, 9-fluorenone-1-carboxylic acid group, benzyloxycarbonyl group, xanthyl group (Xan), trityl group (Trt), 4-methyltrityl group (Mtt), 4-methoxy2,3,6-trimethylbenzenesulfonyl group (Mtr), mesitylene-2-sulfonyl group (Mts), 4,4-dimethoxybenzohydryl group (Mbh), tosyl group (Tos), 2,2,5,7,8-pentamethylchroman-6-sulfonyl group (Pmc), 4-methylbenzyl group (MeBzl), 4-methoxybenzyl group (MeOBzl), benzyloxy group (BzlO), benzyl group (Bzl), benzoyl group (Bz), 3-nitro-2-pyridinesulfenyl group (Npys), 1-(4,4-dimethyl-2,6-diaxocyclohexylidene)ethyl group (Dde), 2,6-dichlorobenzyl group (2,6-DiCl—Bzl), 2-chlorobenzyloxycarbonyl group (2-Cl—Z), 2-bromobenzyloxycarbonyl group (2-Br—Z), benzyloxymethyl group (Bom), cyclohexyloxy group (cHxO), t-butoxymethyl group (Bum), t-butoxy group (tBuO), t-butyl group (tBu), acetyl group (Ac), and trifluoroacetyl group (TFA). From the viewpoint of handleability, Fmoc or Boc is preferred.

From the viewpoint of the labeling with a metal radioactive isotope (metal nuclide), the molecular probe precursor of the present invention may be made of the polypeptide of the formula (4) or (5) in which a chelating site that can be chelating a metal radioactive isotope (metal nuclide) is bonded to an amino group of a side chain of a lysine to which no protecting group is bonded. From the same viewpoint, the molecular probe precursor of the present invention may be made of the polypeptide of the formula (6) in which a chelating site that can be chelating a metal radioactive isotope (metal nuclide) is bonded to an α-amino group at an N-terminus. Examples of the metal nuclide and examples of the compound that can form a chelating site are as described above.

In another embodiment of the present invention, the molecular probe precursor of the present invention includes a polypeptide represented by the formula (4) above (SEQ ID NO. 4) or the formula (5) above (SEQ ID NO. 5) from which 1, 2, 3, 4, 5, 6, or 7 amino acids on the N-terminus side are deleted and that is capable of binding to pancreatic islets after being labeled and deprotected, or a polypeptide that has homology with this polypeptide and that is capable of bonding to pancreatic islets after being labeled and deprotected; and preferably, it includes a molecular probe for imaging of pancreatic islets that consists of the aforementioned polypeptide. In the polypeptide represented by the formula (4) (SEQ ID NO. 4) from which 1, 2, 3, 4, 5, 6, or 7 amino acids on the N-terminus side are deleted, a protecting group for protecting an amino group is bonded an amino group of a side chain of a lysine corresponding to the lysine at position 27 in the polypeptide of the formula (4), and a protecting group for protecting an amino group or a modifying group for modifying an amino group is bonded to an α-amino group at an N-terminus. In the polypeptide of the formula (5) from which 1, 2, 3, 4, 5, 6, or 7 amino acids on the N-terminus side are deleted, a protecting group for protecting an amino group is bonded to an amino group of a side chain of a lysine corresponding to the lysine at position 12 in the polypeptide of the formula (5), and a protecting group for protecting an amino group or a modifying group for modifying an amino group is bonded to an α-amino group at an N-terminus. Examples of polypeptide having homology with the aforementioned polypeptide include the following polypeptides: a polypeptide that is obtained by deletion, insertion, or substitution of one to several amino acids with respect to the polypeptide represented by the formula (4) above (SEQ ID NO. 4) or the polypeptide represented by the formula (5) above (SEQ ID NO. 5) from which 1, 2, 3, 4, 5, 6, or 7 amino acids on the N-terminus side are deleted; and a polypeptide that has homology of 80% or higher with the foregoing polypeptide.

In still another embodiment of the present invention, the molecular probe precursor of the present invention includes a polypeptide represented by the formula (6) above (SEQ ID NO. 6) from which 1, 2, 3, 4, 5, 6, or 7 amino acids on the N-terminus side are deleted and that is capable of binding to pancreatic islets after being labeled and deprotected, or a polypeptide that has homology with this polypeptide and that is capable of bonding to pancreatic islets after being labeled and deprotected; and preferably, it includes a molecular probe for imaging of pancreatic islets that consists of the aforementioned polypeptide. In the polypeptide represented by the formula (6) from which 1, 2, 3, 4, 5, 6, or 7 amino acids on the N-terminus side are deleted, protecting groups for protecting an amino group are bonded an amino group of a side chain of a lysine corresponding to the lysine at position 12 and an amino group of a side chain of a lysine corresponding to the lysine at position 27 in the polypeptide of the formula (6). Examples of polypeptide having homology with the aforementioned polypeptide represented by the formula (6) above (SEQ ID NO. 6) from which 1, 2, 3, 4, 5, 6, or 7 amino acids on the N-terminus side are deleted include the following polypeptides: a polypeptide that is obtained by deletion, insertion, or substitution of one to several amino acids with respect to the polypeptide represented by the formula (6) above (SEQ ID NO. 6) from which 1, 2, 3, 4, 5, 6, or 7 amino acids on the N-terminus side are deleted; and a polypeptide that has homology of 80% or higher with the amino acid sequence of the foregoing polypeptide.

[Method for Producing Molecular Probe for Imaging of the Present Invention]

In still another embodiment of the present invention, the present invention relates to a method for producing a molecular probe for imaging that includes labeling and deprotecting a molecular probe precursor according to the present invention. With the producing method of the present invention, the molecular probe for imaging according to the present invention can be produced.

In the method for producing a molecular probe for imaging according to the present invention, preferably, the molecular probe precursor of the present invention is labeled, and thereafter, it is deprotected by removing a protecting group. Further, the molecular probe precursor of the present invention can be produced by, for example, peptide synthesis in accordance with a typical method such as the Fmoc method, and the peptide synthesis method is not limited particularly.

The labeling can be performed by labeling the molecular probe precursor of the present invention by the method for imaging and/or a known method in accordance with the radioactive nuclide used. The labeling may be performed by, for example, bonding a radioactive nuclide with a compound bondable with an amino group of a side chain of a lysine, and using the same for bonding the radioactive nuclide with the molecular probe precursor according to the present invention. Alternatively, the labeling may be performed by bonding only a radioactive nuclide to the molecular probe precursor according to the present invention. The deprotection can be performed by a known method in accordance with the type of the protective group.

The labeling of the molecular probe precursor preferably includes labeling the molecular probe precursor according to the present invention using a compound containing a radioactive nuclide such as $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, or $^{186}$Re.

Further, the labeling of the molecular probe precursor preferably includes the labeling of the molecular probe precursor of the present invention using the compound having a group represented by the chemical formula (I) shown below. It should be noted that A, $R^1$, $R^2$, and $R^3$ in the chemical formula (I) are as described above.

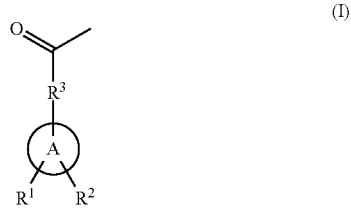

(I)

The compound having the group represented by the chemical formula (I) above preferably is a succinimidyl ester compound in which the group represented by the foregoing chemical formula (I) is bonded with succinimide via ester bond, more preferably, a succinimidyl ester compound represented by the chemical formula (II) shown below. In the succinimidyl ester compound represented by the chemical formula (II) below, it is preferable that A, $R^2$, and $R^3$ represent a phenyl group, a hydrogen atom, and a bond, respectively, since a molecular probe for imaging according to the present invention in which the affinity to pancreatic islets, preferably the affinity to pancreatic β-cells, and more preferably the affinity to GLP-1R of pancreatic β-cells is improved; and it is more preferable that A, $R^1$, $R^2$, and $R^3$ represent a phenyl group, a [$^{18}$F]fluorine atom, a hydrogen atom, and a bond, respectively. In other words, the compound having the group represented by the chemical formula (I) preferably is a succinimidyl ester compound represented by the chemical formula (II) shown below, more preferably a succinimidyl ester compound represented by the chemical formula (IIa) shown below, and further preferably a succinimidyl ester compound ([$^{18}$F]N-succinimidyl 4-fluorobenzoate) represented by the chemical formula (IIb) shown below. It should be noted that A, $R^1$, $R^2$, and $R^3$ in the chemical formula (II) below are identical to those in the case of the chemical formula (I), and $R^1$ in the chemical formula (IIa) is identical to that in the chemical formula (I).

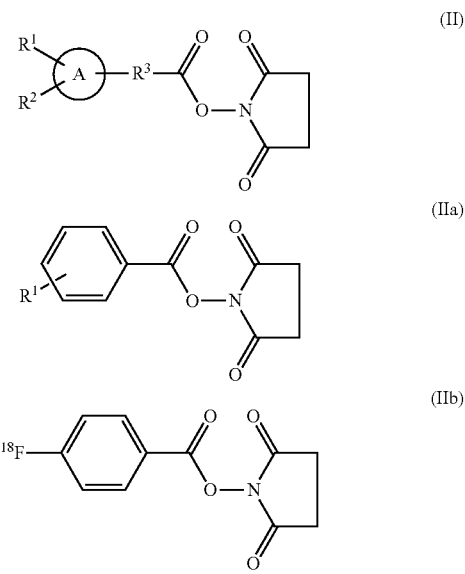

When a radioactive nuclide used in the labeling is $^{123}$I, $^{124}$I, $^{125}$I or $^{131}$I, a labeling compound used in the labeling is preferably, for example, a compound in which $R^1$ in the foregoing formula (IIa) is [$^{123/124/125/131}$I] iodine atom, and more preferably a compound in which $R^1$ is [$^{123/124/125/131}$I] iodine atom and which bonds to the 3-position (meta position). Specifically [$^{123}$I]N-succinimidyl 3-iodobenzoate, [$^{124}$I]N-succinimidyl 3-iodobenzoate, [$^{125}$I]N-succinimidyl 3-iodobenzoate and [$^{131}$I]N-succinimidyl 3-iodobenzoate are preferable.

The method for producing a molecular probe for imaging according to the present invention further may include the step of synthesizing a compound having a group represented by the chemical formula (I), or preferably, a compound having a group represented by the chemical formula (II). The synthesis of the chemical compound used in the labeling may be carried out by, for example, using an automatic synthesizing device.

The method for producing the molecular probe for imaging according to the present invention further may include the step of producing the molecular probe precursor according to the present invention. Alternatively, the synthesis of the labeling compound having the group represented by the foregoing chemical formula (I) and the labeling and deprotecting of a molecular probe precursor in which the foregoing labeling compound is used may be carried out by a single automatic synthesizing device.

In another embodiment of the present invention, the method for producing the molecular probe for imaging of the present invention includes: synthesizing a polypeptide having an amino acid sequence represented by the following formula (20) using protecting amino acids in which the α-amino group at the N-terminus and/or a functional group of the side chain is protected by a protecting group deprotecting, in the synthesized polypeptide, the amino group of the side chain of lysine that is not to be radioactively labeled (Deprotection 1); reprotecting the deprotected amino group by a different protecting group from that removed upon the deprotection; deprotecting, in the deprotected and reprotected polypeptide, the amino group of the side chain of lysine or the α-amino group at the N-terminus to be radioactively labeled (Deprotection 2); radioactively labeling the deprotected amino group; and deprotecting the radioactively labeled polypeptide.

(SEQ ID NO. 20)
HGEGTFTSDLSKQMEEEAVRLFIEWLKNGGPSSGAPPPS (20)

In the method for producing the molecular probe for imaging according to the present embodiment, the lysine that is not to be radioactively labeled is deprotected at Deprotection 1 and the lysine or the α-amino group at the N-terminus to be radioactively labeled is deprotected at Deprotection 2. Possible combinations of the lysines and the α-amino group at the N-terminus to be deprotected at Deprotection 1 and Deprotection 2 are as follows:
(1) Deprotection 1: lysine at position 27 (Lys27), Deprotection 2: lysine at position 12 (Lys 12)
(2) Deprotection 1: Lys12, Deprotection 2: Lys 27
(3) Deprotection 1: Lys 12 and Lys 27, Deprotection 2: the α-amino group at the N-terminus.

With the method for producing the molecular probe for imaging according to the present embodiment, it is possible to selectively label only the intended amino group (the amino group of the side chain of the lysine or the α-amino group at the N-terminus). Thus, with the method for producing the molecular probe for imaging according the present embodiment, it is possible to improve the labeling efficiency and also to increase the yield of the radioactively labeled peptide as desired.

First, a polypeptide having an amino acid sequence represented by the formula (20) is synthesized.

The peptide synthesis can be carried out by, for example, a known organic-chemical peptide synthesis method, and the peptide synthesis can be performed based on descriptions made in, for example, the Japanese Biochemical Society (eds.) "*Seikagaku Jikken Koza* (Lecture on Biochemical Experiment)", Vol, 1 "Protein IV" pp. 207 to 495, (1977, Tokyo Kagaku Dojin) and the Japanese Biochemical Society (eds.) "*Shin-Seikagaku Jikken Koza* (New Lecture on Biochemical Experiment)", Vol. 1 "Protein IV" pp. 3 to 74 (1992, Tokyo Kagaku Dojin).

Examples of organic-chemical peptide synthesis methods include the peptide solid-phase synthesis method, and the peptide liquid-phase synthesis method, among which the peptide solid-phase synthesis method is preferred. In the present specification, the "peptide solid-phase synthesis method" refers to a method in which the C-terminus of an amino acid or a peptide is fixed to a solid-phase carrier via a linker, and amino acids are extended one by one toward the N-terminus. Examples of the peptide solid-phase synthesis method include the Fmoc method and the Boc method, among which the Fmoc method is preferred. In the present specification, the "Fmoc method" refers to a method wherein amino acids with the α-amino group at the N-terminus being protected by Fmoc (9-fluorenylmethyloxycarbonyl group) are used, and they are condensed, so as to synthesize a peptide. More specifically, an amino acid corresponding to the C-terminus of a peptide to be synthesized, or a peptide including an amino acid corresponding to the C-terminus of a peptide to be synthesized, is bonded to a solid-phase carrier such as a resin, the deprotection of the α-amino group at the N-terminus by removing the Fmoc group as a protecting group for the α-amino group at the N-terminus and the washing, and the condensation of the protecting amino acids and the washing, are carried out repeatedly, whereby a peptide chain is extended. In the end, a final deprotection reaction is caused, whereby an intended peptide can be synthesized. For example, an automatic peptide synthesizing device may be used in the peptide synthesis. Examples of the automatic peptide synthesizing device include the A443A type (produced by Applied Biosystems), and PSSM8 (produced by Shimadzu Corporation).

When carrying out the peptide synthesis by the Fmoc method, an Fmoc-amino acid derivative used in a conventional Fmoc-peptide synthesis method can be used as a protecting amino acid used in the peptide synthesis. Specifically, for an amino acid (His, Asp, Ser, Lys, Gln, Glu, Arg, Asn, Trp) with a functional group on its side chain, it is possible to use any amino acid in which a functional group is protected by a protecting group depending on the type of the functional group and the α-amino group at the N-terminus is protected by Fmoc. And for other amino acids, it is possible to use any amino acid in which the α-amino group at the N-terminus is protected by Fmoc.

As the lysine to be deprotected at Deprotection 1 (lysine that is not to be radioactively labeled), from the viewpoint of selective deprotection, it is preferable to use lysine in which the amino group of the side chain is protected by a different protecting group from that for the amino group of the side chain of the lysine or the α-amino group at the N-terminus to be radioactively labeled. For example, when lysine with the amino group of the side chain being protected by a carbamate-type protecting group other than Fmoc is used as the lysine to be radioactively labeled, lysine in which the amino group of its side chain is protected by a trityl-type protecting group may be used as the lysine to be deprotected at Deprotection 1. Examples of carbamate-type protecting groups other than Fmoc include Boc, Cbz, Alloc and Troc, among which Boc is preferred. Examples of trityl-type protecting groups include Mmt, Trt, Mtt and Mtr. From the viewpoint of more selective deprotection, Mmt and Mtt are preferred.

Next, Deprotection 1 and reprotection are carried out.

For example, it is preferable that Deprotection 1 is carried out without deprotecting the amino group of the side chain of the lysine to be deprotected at Deprotection 2. When the lysine to be deprotected at Deprotection 1 is Lys27, it is preferable that only the amino group of the side chain of Lys27 is selectively deprotected without deprotecting other functional groups. When the protecting group for the amino group of the side chain of the lysine to be deprotected is of a trityl-type, for example, it can be removed under weak acid conditions to selectively deprotect the amino group of the side chain of the intended lysine. A reagent making the weak acid conditions is, for example, a reagent containing trifluoroacetic acid.

The reprotection includes, for example, protecting the amino group of the side chain of the deprotected lysine by a different protecting group from the removed protecting group, preferably protecting the amino group by the protecting group for the α-amino group at the N-terminus used in the peptide synthesis, and more preferably protecting the amino group by Fmoc. For example, Fmoc can be introduced by reacting an Fmoc reagent with the amino group of the side chain of the deprotected lysine in the presence of amine. Examples of the Fmoc reagent include N-(9-fluorenyl-methoxy carbonyloxy) succinimide (Fmoc-Osu) and 9-fluorenyl carbinyl chloride (Fmoc-Cl).

Further, if needed, the α-amino group at the N-terminus of the aforementioned polypeptide can be deprotected and reprotected at the time of carrying out the deprotection and the reprotection.

Thereafter, Deprotection 2 is carried out. As a result, the probe precursor to be radioactively labeled can be obtained.

At Deprotection 2, at least the amino group to be radioactively labeled may be deprotected. From the viewpoint of simplifying the deprotecting operation after the radioactive labeling, it is preferable to deprotect the functional groups other than the amino group of the side chain of the deprotected lysine at Deprotection 1 and, if needed, the α-amino group at the N-terminus. As a result, polypeptides (probe precursors) represented by the formulas (4) to (6) can be obtained. The deprotection can be conducted by a known method depending on the type of the protecting group to be removed. This deprotection may be carried out upon the excision of the peptide from a solid-phase carrier, and for example, the above-described deprotection by removing the protecting group may be carried out under the condition for the excision of the peptide.

Thereafter, the deprotected amino group is radioactively labeled. Since the polypeptide (probe precursor) to be radioactively labeled is in such a condition that the amino group to be radioactively labeled is deprotected and other amino groups are protected, it is possible to selectively and radioactively label only the intended amino group (the amino group of the side chain of the lysine or the α-amino group at the N-terminus).

The radioactive labeling can be conducted in accordance with a known method depending on the type of the peptide to be radioactively labeled. Though the labeling compound used in the radioactive labeling is not limited particularly, it may be, for example, the labeling compound having the group represented by the chemical formula (I), or a chelate compound chelatable to a metal radioactive isotope (metal nuclide). Examples of the metal nuclide include $^{64}Cu$, $^{67}Ga$, $^{68}Ga$, $^{82}Rb$, $^{99m}Tc$, $^{111}In$, and $^{186}Re$. Examples of the chelate compound include DTPA, HYNIC, DOTA, DTS, DADT, MAG3, MAMA, DADS, and PnAO. From the viewpoint of production of the molecular probe for imaging of the present invention, the labeling compound is preferably the labeling compound having the group represented by the formula (I), more preferably, the succinimidyl ester compound represented by the formula (II), and still more preferably, a succinimidyl ester compound represented by the formula (IIa).

Finally, the remaining protecting groups in the thus radioactively labeled polypeptide are removed. As a result, polypeptide in which the intended amino group is radioactively labeled can be produced. The deprotection can be conducted in accordance with a known method depending on the type of the protecting groups. In the case where the protecting groups are Fmoc, the deprotection can be carried out, for example, under a piperidine condition.

From the viewpoint of producing radioactively-labeled peptide with a high purity, the method for producing the molecular probe for imaging of the present invention may further include a purification step. The purification step can be carried out, for example, between Deprotection 2 and the radioactive labeling, between the radioactive labeling and the subsequent deprotection (final deprotection), and after the final deprotection. Further, the method for producing the molecular probe for imaging of the present invention may include a step of modifying the α-amino group at the N-terminus of the radioactively labeled polypeptide with a modifying group having no electric charge, or a step of amidating the carboxyl group at the C-terminus.

[Method for Imaging]

Still another aspect of the present invention relates to a method for imaging of pancreatic islets that includes imaging pancreatic islets using the molecular probe for imaging of the present invention. Still another aspect of the present invention relates to a method for imaging of pancreatic islets that includes detecting a signal of the molecular probe for imaging from an analyte to which the molecular probe for imaging according the present invention has been administered. With the method for imaging of the present invention, in which the molecular probe for imaging according to the present invention is used, pancreatic islets, or preferably, pancreatic β-cells, can be imaged. The method for imaging of the present invention can be carried out by detecting a signal of the molecular probe for imaging according to the present invention from an analyte to which the molecular probe for imaging of the present invention has been administered, a certain period of time since the administration of the molecular probe. Examples of the analyte include humans, and mammals other than humans. The detection of the signal of the molecular probe for imaging includes, for example, detecting a signal of a radioactive nuclide used for labeling the molecular probe for imaging.

The method for imaging of the present invention may include reconfiguring the detected signal so as to convert the same into an image, and further may include displaying the image obtained by the conversion.

In the method for imaging of the present invention, the detection of the signal may be determined appropriately according to the type of the radioactive nuclide of the molecular probe used, and may be carried out by the determination using PET, the determination using SPECT, etc.

The determination by means of SPECT includes, for example, determining, with use of a gamma camera, γ-rays emitted from an analyte to which the molecular probe for imaging of the present invention has been administered. The determination with use of the gamma camera includes, for example, measuring radiation (γ-rays) emitted from the radioactive nuclides used for labeling the molecular probe for imaging of the present invention during a certain time unit, and preferably includes determining a direction in which the radiation is emitted and a radiation dose during a certain time unit. The method for imaging according to the present invention further may include presenting the determined distribution of the molecular probe for imaging of the present invention obtained by the measurement of the radiation as a cross-sectional image, and reconfiguring the obtained cross-sectional image.

The determination by means of PET include, for example, simultaneously measuring γ-rays generated upon annihilation of positrons with electrons, with use of a detector for PET, from an analyte to which the molecular probe for imaging of the present invention has been administered, and further may include figuring a three-dimensional distribution of positions of radioactive nuclides emitting positrons, based on the measurement results.

In the method for imaging according to the present invention, the determination by means of X-ray CT or MRI may be performed, together with the determination by means of SPECT or the determination by means of PET. This makes it possible to obtain, for example, a fusion image obtained by fusion of an image obtained by SPECT or an image obtained by PET (functional image), with an image obtained by CT or an image obtained by MRI (morphological image).

The method for imaging according to the present invention may include determining a state of pancreatic islets based on the results of the imaging of pancreatic islets with use of the molecular probe for imaging according to the present invention. Determining a state of pancreatic islets based on the results of the imaging of pancreatic islets with use of the molecular probe includes, for example, determining the presence/absence of pancreatic islets by analyzing an image of the imaging of pancreatic islets, and determining an increase/decrease in the amount of pancreatic islets.

The method for imaging of the present invention may include administering the molecular probe for imaging of the present invention to an analyte, and the administration of the molecular probe for imaging of the present invention to an analyte preferably is carried out by administering the molecular probe in an enough amount to obtain a desired contrast for imaging. The administration to an analyte may be local administration or systemic administration. A path for administration may be determined appropriately according to a state of an analyte and the like, and it may be, for example, intravenous, intraarterial, intradermal, and intraabdominal injection or infusion.

The molecular probe for imaging of the present invention preferably is administered together with a medicinal additive such as a carrier. In the present specification, the "medicinal additive" refers to a chemical compound that has obtained authorization as a medicinal additive in the Japanese, U.S. and/or European pharmacopoeias. Examples of the carrier include aqueous solvents and non-aqueous solvents. Examples of the aqueous solvent include potassium phosphate buffer solution, physiologic saline, Ringer solution, and distilled water. Examples of the non-aqueous solvent include polyethylene glycol, vegetable fats and oils, ethanol, glycerol, dimethyl sulfoxide, and propylene glycol. The amount of the molecular probe of the present invention for imaging of pancreatic islets or determining an amount of pancreatic islets may be set to be, for example, not more than 1 μg. The time period from the administration to the determination may be decided appropriately according to, for example, a time that it takes for the molecular probe to be bound to pancreatic islets, the type of the molecular probe, the decomposition time of the molecular probe, etc.

[Method for Determining Amount of Pancreatic Islets]

Still another aspect of the present invention relates to a method for determining an amount of pancreatic islets, including detecting a signal of the molecular probe for imaging of the present invention from an analyte to which the molecular probe for imaging of the present invention has been administered, and calculating an amount of the pancreatic islets from the detected signal of the molecular probe for imaging. Still another aspect of the present invention relates to a method for determining an amount of pancreatic islets, the method including imaging pancreatic islets using the molecular probe for imaging according to the present invention, and calculating an amount of pancreatic islets from results of the imaging.

The calculation of the amount of pancreatic islets can be carried out by, for example, analyzing the detected signal amount, and an image obtained by reconfiguration of the signal. Further, the quantification of a subject of the imaging from results of the imaging can be performed easily by any person skilled in the art, using a calibration curve, an appropriately program, or the like. The subject of imaging is, for example, pancreatic islets, and preferably pancreatic β-cells, and more preferably GLP-1R of pancreatic β-cells. The method for determining an amount of pancreatic islets according to the present invention preferably is a method for determining an amount of pancreatic β-cells from the viewpoint of the application of the same to the examination and diagnosis.

The method for determining an amount of pancreatic islets according to the present invention further may include presenting the calculated amount of pancreatic islets. Presenting the calculated amount of pancreatic islets includes, for example, storing the calculated amount of pancreatic islets or outputting the same to the outside. Outputting the same to the outside includes, for example, displaying the same on a monitor and printing the same.

[Methods for Prevention, Treatment, and Diagnosis of Diabetes]

Still another aspect of the present invention relates to a method for prevention, treatment, or diagnosis of diabetes. As described above, in the diabetes developing process, the amount of pancreatic islets (particularly, the amount of pancreatic β-cells) decreases prior to the occurrence of glucose tolerance abnormalities, and therefore, when functional abnormalities are detected or there are subjective symptoms, diabetes has already reached the stage where it is too difficult to be treated. With the method for imaging using the molecular probe for imaging according to the present invention and/or the method for determining an amount of the pancreatic islets using the same, however, a decrease in the amount of the pancreatic islets and/or the amount of the pancreatic β-cells can be detected at an early stage, and further, new methods for prevention, treatment, and diagnosis of diabetes can be created. Examples of a subject on which prevention, treatment, and diagnosis of diabetes is carried out include humans and/or mammals other than humans.

A method for diagnosis of diabetes according to the present invention may include imaging of pancreatic islets with use of the molecular probe for imaging of the present invention; and determining a state of the pancreatic islets based on the obtained image of the pancreatic islets and/or the obtained amount of the pancreatic islets, and performing diagnosis of diabetes based on the determination results. The determination of a state of pancreatic islets includes, for example, determining an increase/decrease, or a change, in the amount of pancreatic islets by comparing the obtained image of pancreatic islets with an image of pancreatic islets as a reference, or comparing the obtained amount of pancreatic islets with an amount of pancreatic islets as a reference. Further, the determination of a state of pancreatic islets may be carried out using an information processing device. When it is determined that the amount of pancreatic islets has decreased, preferably this information is presented, and when it is determined that the amount of pancreatic islets has increased or has been maintained, preferably this information is presented. The diagnosis of diabetes on the basis of the determination results includes, for example, determining a risk of development of diabetes, judging it to be diabetes, and determining a degree of development of diabetes.

A method for treatment of diabetes of the present invention includes imaging of pancreatic islets with use of the molecular probe for imaging of the present invention, determining a state of pancreatic islets on the basis of the obtained image of the pancreatic islets and/or the obtained amount of the pancreatic islets so as to perform diagnosis of diabetes, and treating diabetes on the basis of the diagnosis. The determination of a state of pancreatic islets and the diagnosis of diabetes can be performed in the same manner as those in the method for diagnosis of diabetes according to the present invention. The method for treatment of diabetes according to the present invention may include evaluating an effect of treatment such as medication and diet performed on a subject, focusing on a change in an amount of pancreatic islets.

A method for prevention of diabetes of the present invention includes imaging of pancreatic islets with use of the molecular probe for imaging of the present invention, and determining a state of pancreatic islets on the basis of the obtained image of the pancreatic islets and/or the obtained amount of the pancreatic islets so as to determine a risk of development of diabetes. The method for prevention of diabetes of the present invention may include regularly determining an amount of pancreatic islets, and checking presence/absence of a tendency of a decrease in the amount of pancreatic islets.

Still another preferable aspect of the present invention relates to a method for ultra-early diagnosis of diabetes. The method for ultra-early diagnosis of diabetes of the present invention may include, for example, imaging pancreatic islets or determining an amount of pancreatic islets in comprehensive or ordinary medical examination by the method of the present invention, and determining a state of the pancreatic islets on the basis of the obtained image of the pancreatic islets or the determined amount of the pancreatic islets. Further, a method for treatment of diabetes of the present invention may include imaging pancreatic islets and/or determining an amount of pancreatic islets by the method of the present invention, and evaluating functional recovery of the pancreatic islets on the basis of the obtained image of the pancreatic islets and/or the determined amount of the pancreatic islets.

[Kit of the Present Invention]

Still another aspect of the present invention also relates to a kit including the molecular probe for imaging of the present invention. Examples of embodiments of the kit of this aspect include a kit for performing the method for imaging of the present invention, a kit for performing the method for determining an amount of pancreatic islets according to the present invention, and a kit for prevention, treatment, or diagnosis of diabetes according to the present invention. Preferably, in each of these embodiments, the kit includes an instruction manual suitable for the embodiment.

In the kit of the present invention, the molecular probe for imaging of the present invention included in the kit preferably is in a form of a parenteral solution. Therefore, the kit of the present invention preferably includes a parenteral solution that contains the molecular probe for imaging of the present invention. The parenteral solution may contain the molecular probe for imaging of the present invention as an effective ingredient, and further, for example, a medicinal additive such as a carrier. The medicinal additive and the carrier are as described above.

The kit of the present invention further may include a container for containing the molecular probe for imaging of the present invention, and the container may be filled with the molecular probe for imaging of the present invention and/or a parenteral solution that contains the molecular probe for imaging of the present invention. Examples of the container include a syringe and a vial.

The kit of the present invention may further include, for example, a component used for preparing a molecular probe, such as a buffer or an osmotic regulator, and an instrument used in administration of a molecular probe, such as a syringe.

[Reagent for Imaging of the Present Invention]

Still another aspect of the present invention relates to a reagent for imaging, the reagent containing the molecular probe for imaging according to the present invention. The reagent for imaging according to the present invention contains a molecular probe for imaging according to the present invention as an effective ingredient, and further may contain a medical additive such as a carrier. The carrier is as described above.

[Another Aspect of the Kit of the Present Invention]

Still another aspect of the present invention relates to a kit including the aforementioned molecular probe precursor. Examples of embodiments of the kit including the molecular probe precursor of the present invention include a kit for preparing the molecular probe for imaging of the present invention, a kit for performing the method for imaging of the present invention, a kit for performing the method for determining an amount of pancreatic islets according to the present invention, and a kit for prevention, treatment, or diagnosis of diabetes according to the present invention. Preferably in each of these embodiments, the kit including the molecular probe precursor of the present invention includes an instruction manual suitable for each embodiment.

The form of the molecular probe precursor of the present invention included in the kit is not particularly limited, and may be in the form of solution or powder, for example. In terms of handling, the molecular probe precursor is preferably in the form of powder, and more preferably in the form of freeze-dried powder (freeze-dried formulation).

The kit including the molecular probe precursor according to the present invention may include, for example, a compound used in the labeling of the precursor of the molecular probe for imaging, the compound having the group represented by the aforementioned chemical formula (I). The compound having the group represented by the chemical formula (I) preferably is a succinimidyl ester compound in which the group represented by the foregoing chemical formula (I) is bonded with succinimide via ester bond, more preferably, a succinimidyl ester compound represented by the aforementioned chemical formula (II), and further more preferably, a succinimidyl ester compound represented by the aforementioned chemical formula (IIa). The kit of the present embodiment more preferably includes, in particular, [$^{18}$F]N-succinimidyl 4-fluorobenzoate, or a starting material for [$^{18}$F]N-succinimidyl 4-fluorobenzoate, as a labeling compound. Examples of the foregoing starting material include ethyl 4-(trimethylammonium triflate)benzoate, ethyl 4-(tosyloxy)benzoate, and ethyl 4-(methylsulfonyloxy)benzoate. The kit of the present embodiment further may include, for example, an instruction manual that describes the method for labeling the molecular probe precursor of the present invention in which the above-described compound is used.

The kit including the molecular probe precursor of the present invention preferably includes a labeling compound such as [$^{123}$I]N-succinimidyl 3-iodobenzoate, [$^{124}$I]N-succinimidyl-3-iodobenzoate, [$^{125}$I]N-succinimidyl 3-iodobenzoate, and/or [$^{131}$I]N-succinimidyl 3-iodobenzoate or the starting materials thereof. Examples of the starting materials include 2,5-dioxopyrrolidin-1-yl3-(tributylstannyl)benzoate, 2,5-dioxopyrrolidin-1-yl 3-bromobenzoate, 2,5-dioxopyrrolidin-1-yl 3-chlorobenzoate, and 2,5-dioxopyrrolidin-1-yl 3-iodobenzoate.

The kit including the molecular probe precursor of the present invention further may include, for example, a reagent to be used for deprotecting the molecular probe for imaging and/or a reagent to be used for labeling the molecular probe.

The kit including the molecular probe precursor of the present invention further may include, for example, an automatic synthesizing device for synthesizing the labeling compound, and an instruction manual that describes a method for synthesizing the compound having a group represented by the aforementioned chemical formula (I) using the foregoing automatic synthesizing device for synthesizing the labeling compound. The automatic synthesizing device may be capable of synthesizing the labeling compound, and further, for example, capable of labeling and deprotecting the molecular probe precursor in which the synthesized labeling compound is used. The kit further may include, for example, a reagent containing a radioactive nuclide to be used in synthesizing the labeling compound. Examples of the reagent containing a radioactive nuclide include reagents containing radioactive isotopes such as $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, and $^{186}$Re.

Still another aspect of the present invention relates to a kit that includes an automatic peptide synthesizing device for synthesizing the molecular probe precursor of the present invention, and the labeling compound having the group represented by the aforementioned chemical formula (I) and/or an automatic synthesizing device for synthesizing the labeling compound. The automatic synthesizing device may be capable of synthesizing the labeling compound, and further, for example, capable of labeling and deprotecting the molecular probe precursor in which the synthesized labeling compound is used. The kit may include an instruction manual that describes a method for synthesizing the molecular probe precursor of the present invention. The instruction manual further may describe, for example, a method for synthesizing the compound having a group represented by the aforementioned chemical formula (I), a labeling method using the same, and a deprotecting method using the same. The kit further may include a reagent containing a radioactive nuclide to be used in synthesis of a labeling compound.

Still another aspect of the present invention relates to a kit that it includes the following: an automatic synthesizing device that performs the synthesis of t molecular probe of the present invention, the synthesis of the aforementioned labeling compound, and the labeling and deprotecting of the aforementioned molecular probe precursor in which the aforementioned labeling compound is used; and an instruction manual that describes a method for producing a molecular probe for imaging of the present invention with use of the foregoing automatic synthesizing device. The instruction manual preferably describes, for example, a method for synthesizing a molecular probe precursor, a method for synthesizing the aforementioned labeling compound, and a method for labeling and deprotecting the molecular probe precursor in which the aforementioned labeling compound is used. The kit further may include a reagent containing a radioactive nuclide to be used in synthesis of the labeling compound.

[Other Applications]

The sequence of the amino acids in the foregoing formula (1) (SEQ ID NO. 1 in the Sequence Listing) and the sequence of the amino acids in the foregoing formula (2) (SEQ ID NO. 2 in the Sequence Listing) are identical to the amino acid sequence of exendin-4 except for a lysine residue labeled with a radioactive nuclide. Further, the sequence of the amino acids in the foregoing formula (3) (SEQ ID NO. 3 in the Sequence Listing) is identical to the amino acid sequence of exendin-4 except for an α-amino group at an N-terminus labeled with a radioactive nuclide. It is known that exendin-4 is an analog of GLP-1, and bonds to GLP-1R expressed on the pancreatic β-cell. Therefore, the molecular probes including the polypeptides represented by the formulae (1) to (3) and polypeptides having homology with the foregoing polypeptides are bondable to GLP-1R, and preferably bondable specifically to GLP-1R, and therefore, they can be used in the imaging and quantification of GLP-1R-positive cells, and diagnosis and treatment of diseases involving the expression of GLP-1R. Therefore, the "pancreatic islets" described above in the present specification can be interpreted as "GLP-1R-positive cells", and with the present invention, it is possible to perform the imaging and quantification of GLP-1R-positive cells, like the imaging, quantification, and the like of the pancreatic cells, as well as to perform the diagnosis, treatment, and the like of the diseases involving the expression of GLP-1R. The disease involving the expression of GLP-1R is, for example, a neuroendocrine tumor (NET). Examples of the neuroendocrine tumor include insulinoma, small cell bronchial carcinoma, and pancreatic cancer.

Hereinafter, the present invention will be described further by way of Examples and Reference Examples. It should be noted that the present invention is, when interpreted, not limited to the following Examples.

In the description of the present specification, the following abbreviations are used.

OBu: butyl ester group
Boc: butoxycarbonyl group
Trt: trityl group
Pdf 2,2,4,6,7-pentamethyldihydrobenzofuran-5-sulfonyl group
Mmt: 4-methoxytrityl group
Fmoc: 9-fluorenylmethyloxycarbonyl group

EXAMPLES

Example 1

Preparation of Molecular Probe

A molecular probe of the formula (7) below (SEQ ID NO. 7) was prepared that had a configuration in which an amino group of a side chain of a lysine residue at position 12 was labeled with [$^{18}$F]fluorobenzoyl (hereinafter referred to also as "[$^{18}$F]FB label") and a carboxyl group at a C-terminus is amidated in the sequence of SEQ ID NO. 1.

(7)

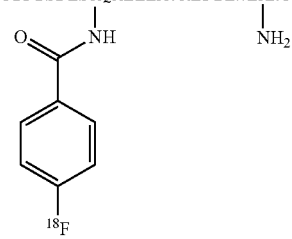

Polypeptide synthesis was performed by using an automatic peptide synthesizer (Model 433A) manufactured by Applied Biosystems, in accordance with the attached software. For the amino acids having functional groups at the side chains, His(Trt), Asp(OBu), Ser(OBu), Lys(Boc), Gln(Trt), Glu(OBu), Arg(Pbf), Asn(Trt) and Trp(Boc) were used respectively. For the lysine at position 27, Lys(Mmt) was used. Rink Amide MBHA (0.125 mmol, 0.34 mmol/g) was employed as the starting resin, the amino acids were extended serially according to the sequence, whereby the polypeptide having the sequence of the following formula (8) was obtained. In the following formula (8), the protecting groups of the side chains other than Lys(Mmt) were not recited.

(SEQ ID NO. 8)
Fmoc-HGEGTFTSDLSKQMEEEAVRLFIEWLK(Mmt)NGGPSSGAPPPSresin (8)

By a typical process using 1.5% TFA—5% TIS—93.55% $CH_2Cl_2$, the protecting group (Mmt groups) of the side chain of the lysine residue at position 27 was removed from the polypeptide of the above formula (8), and the amino group of the side chain of the free lysine residue at position 27 was Fmoc-bonded. Subsequently, removal of all of the protecting groups other than the Fmoc group of the lysine residue at position 27 and the Fmoc group of the α-amino group at the N-terminus, and excision of peptide from the resin, were carried out by a typical process using 92.5% TFA—2.5% TIS—2.5% $H_2O$—2.5% ethanediol. After completion of the reaction, the carrier resin was removed by filtration, and dry ether was added thereto for precipitating the crude product, which was then filtered. The thus obtained crude product was purified in a linear gradient system of $CH_3CN$—$H_2O$ containing 0.1% TFA, using a Liquid Chromatograph LC8A manufactured by Shimadzu Corp. (ODS column 3 cm×25 cm). Then, intended fractions were collected by using a fraction collector, and thus the molecular probe precursor of the following formula (9) was obtained as a lyophilized white powder.

(SEQ ID NO. 9)
Fmoc-HGEGTFTSDLSKQMEEEAVRLFIEWLK(Fmoc)

NGGPSSGAPPPS-$NH_2$ (9)

The thus obtained molecular probe precursor (560 μg) of the above-described formula (9) was dissolved in borate buffer (pH 7.8). [$^{18}$F]N-succinimidyl 4-fluorobenzoate ([$^{18}$F] SFB) was added thereto so that pH of the reaction solution was adjusted to 8.5 to 9.0. Thus, the precursor was labeled. Thereafter, DMF and piperidine were added thereto so as to cause a deprotecting reaction, whereby the intended molecular probe of the above-described formula (7) (molecular probe having a configuration in which the lysine residue at position 12 was labeled in the sequence of SEE ID NO. 1) was obtained. It should be noted that the α-amino group at the N-terminus is not modified in the molecular probe of the foregoing formula (7).

[Biodistribution]

Figure 1A:
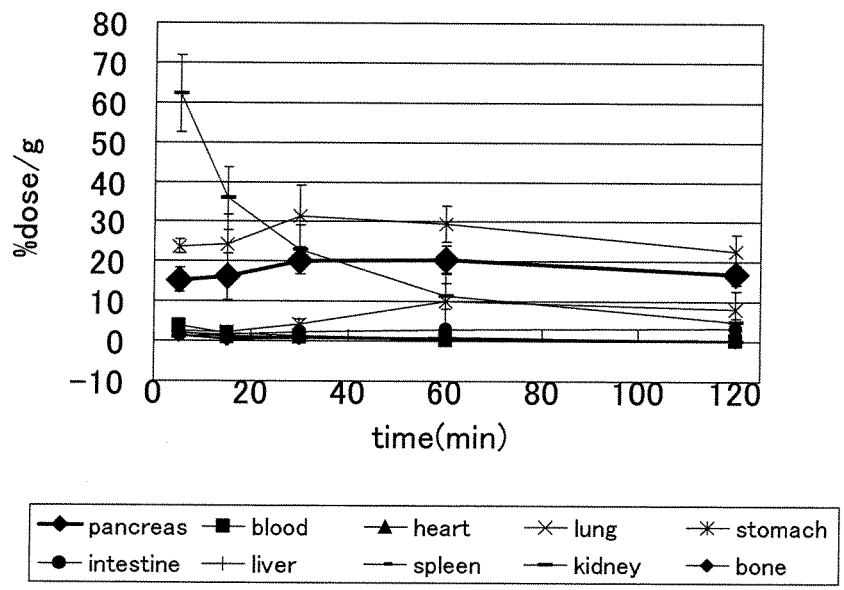
FIGS. 1A and 1B are graphs showing exemplary variations with time in biodistribution of a molecular probe for imaging according to Example 1.
Figure 1B:
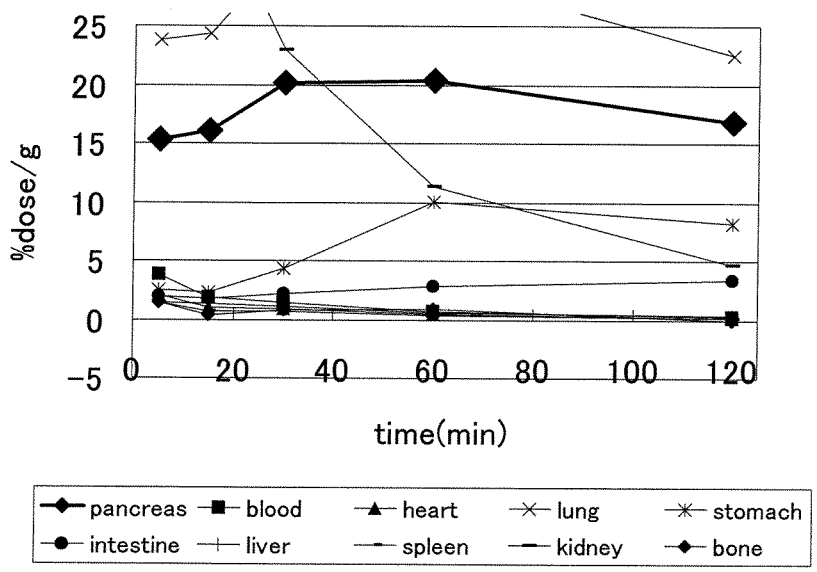
Figure 2A:
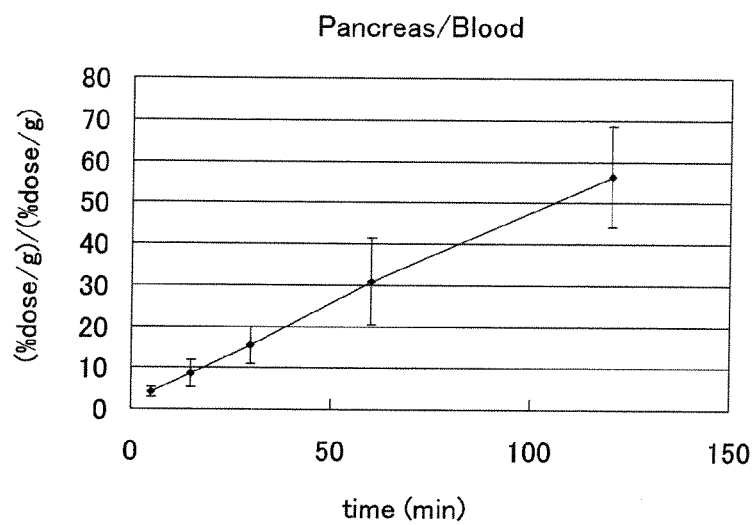
FIGS. 2A to 2C are graphs showing exemplary variations with time in biodistribution of the molecular probe for imaging according to Example 1 (pancreas/other organ ratios).
Figure 2B:
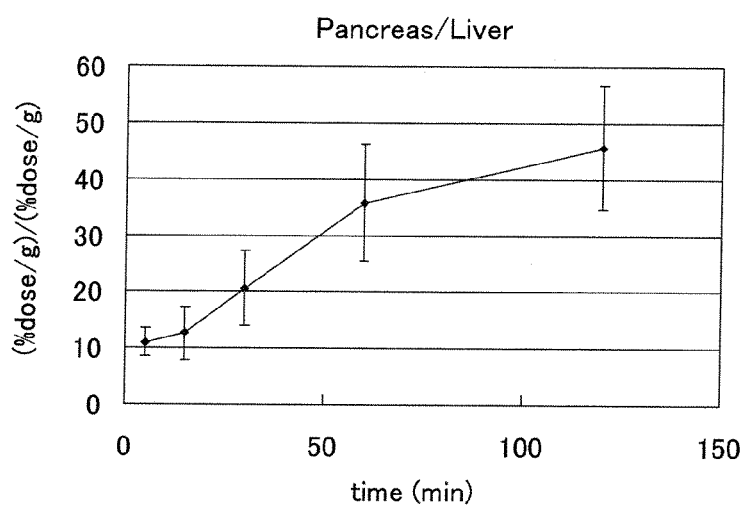
Figure 2C:
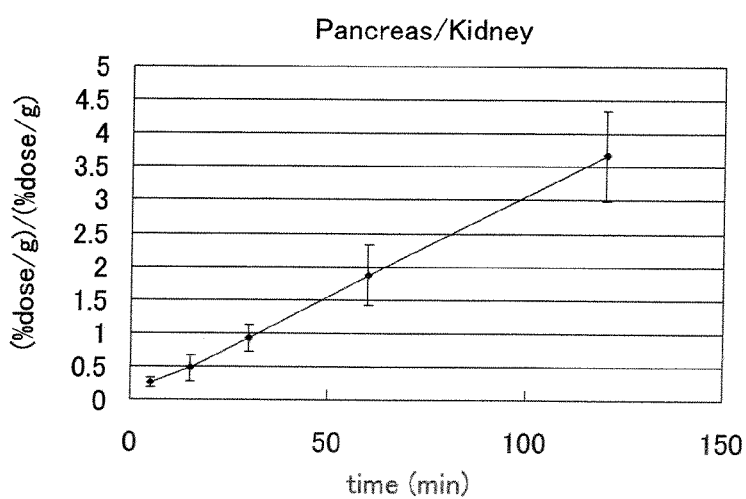

The molecular probe thus prepared (4.2 μCi) of the aforementioned formula (7) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice (n=5). The weight and the radioactivity of each organ were determined, and an accumulation amount (% dose/g) of the probe was calculated from the radioactivity per unit weight. Exemplary results are shown in Table 1 below, FIGS. 1A, 1B, and 2A to 2C. FIGS. 1A and 1B are graphs showing how the accumulation of the molecular probe in each organ varied with time, and FIG. 1B is an enlarged graph of FIG. 1A. FIGS. 2A to 2C are graphs showing resultant variations with time of the accumulation of the molecular probe of Example 1, by pancreas/other organ ratios ((% dose/g)/(% dose/g)).

TABLE 1

| | Time after administration | | | | |
|---|---|---|---|---|---|
| | 5 min | 15 min | 30 min | 60 min | 120 min |
| Pancreas | 15.36 | 16.08 | 20.20 | 20.42 | 16.83 |
| | (3.00) | (5.83) | (1.90) | (3.59) | (2.39) |
| Blood | 3.82 | 1.92 | 1.43 | 0.71 | 0.31 |
| | (0.40) | (0.25) | (0.57) | (0.24) | (0.06) |
| Heart | 2.14 | 1.04 | 0.87 | 0.50 | 0.20 |
| | (0.17) | (0.11) | (0.17) | (0.19) | (0.05) |
| Lung | 23.81 | 24.30 | 31.46 | 29.53 | 22.57 |
| | (1.81) | (7.40) | (7.72) | (4.42) | (4.26) |
| Stomach | 2.53 | 2.28 | 4.39 | 10.03 | 8.23 |
| | (0.44) | (0.84) | (1.00) | (7.15) | (4.29) |
| Intestine | 2.01 | 1.74 | 2.22 | 2.80 | 3.40 |
| | (0.34) | (0.30) | (0.48) | (1.23) | (1.82) |
| Liver | 1.41 | 1.30 | 1.13 | 0.60 | 0.38 |
| | (0.09) | (0.26) | (0.58) | (0.19) | (0.08) |
| Spleen | 1.40 | 0.72 | 0.67 | 0.39 | 0.11 |
| | (0.24) | (0.08) | (0.28) | (0.18) | (0.10) |
| Kidney | 62.04 | 35.89 | 22.97 | 11.38 | 4.73 |
| | (9.72) | (7.91) | (6.16) | (3.28) | (1.20) |
| Bone | 1.40 | 0.36 | 0.79 | 0.89 | −0.03 |
| | (1.00) | (0.22) | (1.01) | (1.04) | (0.27) |

Each numerical value indicates an average (SD) of 5 mice.

As shown in Table 1 and FIG. 1, the accumulation of the molecular probe of the above-described formula (7) into the pancreas was 15.4% dose/g at a point of 5 minutes after the administration, 16.1% dose/g at a point of 15 minutes after the administration, 20.2% dose/g at a point of 30 minutes after the administration, and 20.4% dose/g at a point of 60 minutes after the administration. During a time period from the point of 15 minutes to the point of 30 minutes after the administration, the molecular probe of the foregoing formula (7) accumulated most in the pancreas among the organs other than the lungs and the kidneys. During a time period from the point of 60 minutes after the administration, the molecular probe of the foregoing formula (7) accumulated most in the pancreas among the organs other than the lungs. During a time period from the point of 30 minutes to the point of 60 minutes after the administration, the accumulation of the probe in the pancreas was maintained at a level exceeding 20% dose/g.

Further, as shown in FIG. 2A, the molecular probe of the foregoing formula (7) exhibited a ratio of the accumulation thereof in the pancreas to the accumulation thereof in blood (the pancreas/blood ratio ((% dose/g)/(% dose/g))) that increased with time. The accumulation ratio exceeded 15 at the point of 30 minutes after the administration, and the accumulation ratio exceeded 30 at the point of 60 minutes after the administration. As shown in FIG. 2C, the molecular probe of the foregoing formula (7) exhibited a ratio of the accumulation thereof in the pancreas to the accumulation thereof in the kidney (pancreas/kidney ratio ((% dose/g)/(% dose/g))) that increased with time. The accumulation ratio reached the vicinity of 1 at the point of 30 minutes after the administration, and reached the vicinity of 2 at the point of 60 minutes after the administration.

This suggests that the molecular probe of the foregoing formula (7) allowed, for example, a desired contrast for imaging by PET to be obtained. Besides, as shown in FIG. 1, it was suggested that the molecular probe of the foregoing formula (7) exhibited low radioactivity accumulation in bones, and was not subjected to defluorination metabolism in vivo.

Therefore, the molecular probe of Example 1 represented by the aforementioned formula (7) is considered suitable for the imaging of pancreatic β-cells.

Reference Example 1

For Reference Example 1, a molecular probe was prepared from a molecular probe precursor of the following formula (10) (SEQ ID NO. 10), in which protecting groups (Fmoc) were bonded to an α-amino group at an N-terminus and to the lysine residue at position 19 and a carboxyl group at a C-terminus was amidated. This molecular probe was used for determining biodistribution thereof in a mouse. In other words, using the molecular probe represented by the following formula (11) (SEQ ID NO. 11), having a configuration in which [$^{18}$F] FB was bonded to an amino group of a side chain of a lysine at position 4 and a carboxyl group at a C-terminus was amidated in the amino acid sequence of SEQ ID NO. 10, the biodistribution of this molecular probe in a mouse was determined. Preparation of the molecular probe precursor and the molecular probe and also determination of the biodistribution were carried out in the same manner as Example 1. Exemplary results are shown in Table 2 below and FIG. 3.

(SEQ ID NO. 10)

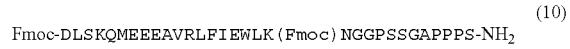

(10)

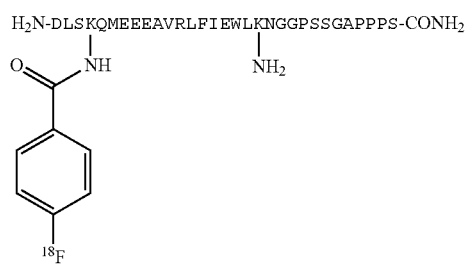

(11)

TABLE 2

| | Time after administration | | | | |
|---|---|---|---|---|---|
| | 5 min | 15 min | 30 min | 60 min | 120 min |
| Pancreas | 3.98 | 4.92 | 4.65 | 2.42 | 1.35 |
| | (0.27) | (0.48) | (1.83) | (0.57) | (0.37) |
| Blood | 9.95 | 5.52 | 4.08 | 1.64 | 0.57 |
| | (0.75) | (0.26) | (0.93) | (0.14) | (0.16) |
| Heart | 4.05 | 2.43 | 1.85 | 0.79 | 0.30 |
| | (0.34) | (0.22) | (0.67) | (0.06) | (0.08) |
| Lung | 8.33 | 5.87 | 4.49 | 2.44 | 1.24 |
| | (0.77) | (0.47) | (0.57) | (0.49) | (0.20) |
| Stomach | 2.18 | 2.11 | 1.09 | 3.27 | 9.08 |
| | (1.28) | (1.08) | (0.43) | (4.79) | (9.78) |
| Intestine | 1.99 | 1.51 | 1.58 | 1.92 | 4.73 |
| | (0.16) | (0.10) | (0.50) | (1.19) | (1.17) |
| Liver | 8.57 | 5.82 | 4.15 | 1.96 | 0.59 |
| | (0.80) | (0.46) | (0.62) | (0.32) | (0.22) |
| Spleen | 3.52 | 2.48 | 1.87 | 0.86 | 0.33 |
| | (0.36) | (0.31) | (0.47) | (0.25) | (0.08) |
| Kidney | 43.16 | 37.86 | 24.10 | 11.25 | 5.27 |
| | (5.40) | (6.69) | (3.82) | (2.52) | (1.88) |
| Bone | 2.41 | 2.01 | 1.36 | 1.07 | 0.32 |
| | (0.17) | (0.18) | (0.33) | (0.73) | (0.18) |

Each numerical value indicates an average (SD) of 5 mice.

Reference Example 2

For Reference Example 2, a molecular probe was prepared from a molecular probe precursor of the following formula (12) (SEQ ID NO. 12), having a configuration in which protecting groups (Fmoc) were bonded to an N-terminus and a lysine residue at position 4 and a carboxyl group at a C-terminus was amidated. This molecular probe was used for determining biodistribution thereof in a mouse. In other words, using the molecular probe represented by the following formula (13) (SEQ ID NO. 13), having a configuration in which [$^{18}$F] FB was bonded to an amino group of a side chain of a lysine at position 19 and a carboxyl group at a C-terminus was amidated in the amino acid sequence of SEQ ID NO. 12, biodistribution of this molecular probe in a mouse was determined. Preparation of the molecular probe precursor and the molecular probe and also determination of the biodistribution were carried out in the same manner as Example 1. Exemplary results are shown in Table 3 below and FIG. 4.

(SEQ ID NO. 12)

(12)

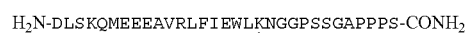

(13)

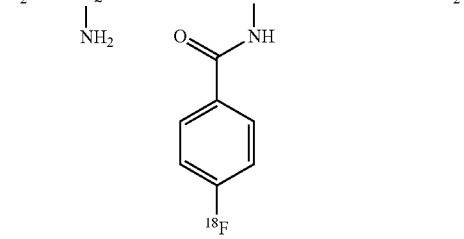

TABLE 3

| | Time after administration | | | | |
|---|---|---|---|---|---|
| | 5 min | 15 min | 30 min | 60 min | 120 min |
| Pancreas | 3.97 | 4.13 | 3.92 | 3.32 | 1.64 |
| | (0.89) | (0.56) | (0.51) | (1.16) | (0.15) |
| Blood | 8.84 | 6.34 | 4.40 | 2.66 | 1.42 |
| | (0.49) | (1.41) | (0.54) | (0.74) | (0.13) |
| Heart | 3.56 | 2.92 | 1.82 | 1.09 | 0.63 |
| | (0.38) | (0.61) | (0.21) | (0.28) | (0.08) |
| Lung | 7.56 | 6.60 | 5.62 | 3.46 | 2.33 |
| | (1.14) | (0.47) | (0.31) | (0.56) | (0.28) |
| Stomach | 0.87 | 1.09 | 1.04 | 1.16 | 1.00 |
| | (0.12) | (0.20) | (0.21) | (0.54) | (0.66) |
| Intestine | 1.29 | 1.25 | 1.04 | 1.47 | 2.09 |
| | (0.19) | (0.36) | (0.19) | (0.25) | (0.54) |
| Liver | 25.23 | 16.81 | 11.71 | 7.56 | 3.72 |
| | (3.40) | (1.90) | (2.74) | (1.63) | (0.58) |
| Spleen | 3.06 | 2.42 | 1.81 | 1.22 | 0.75 |
| | (0.79) | (0.23) | (0.34) | (0.28) | (0.23) |
| Kidney | 30.30 | 38.04 | 29.70 | 17.14 | 11.35 |
| | (3.53) | (7.06) | (5.57) | (4.74) | (4.10) |
| Bone | 1.87 | 1.65 | 1.23 | 0.89 | 0.56 |
| | (0.12) | (0.21) | (0.23) | (0.16) | (0.15) |

Each numerical value indicates an average (SD) of 5 mice.

Figure 3A:
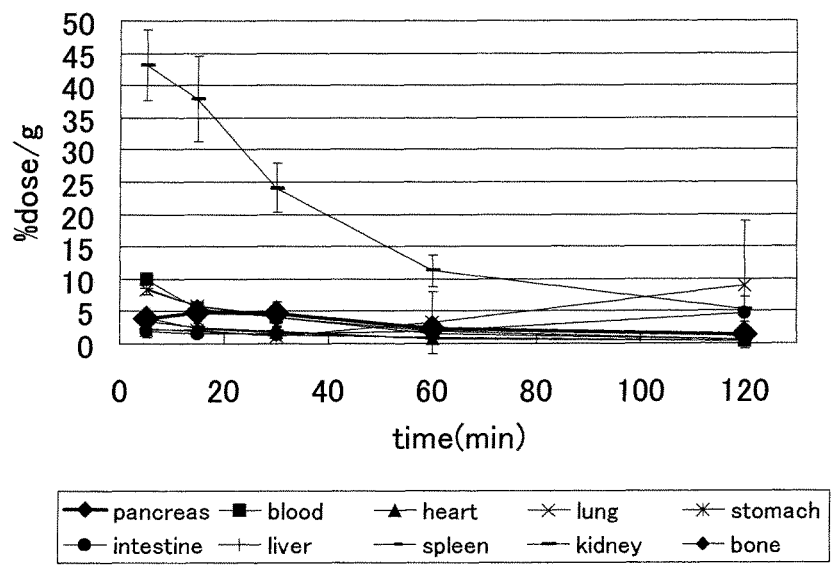
FIGS. 3A and 3B show exemplary resultant variations with time in biodistribution of a molecular probe of Reference Example 1.
Figure 3B:
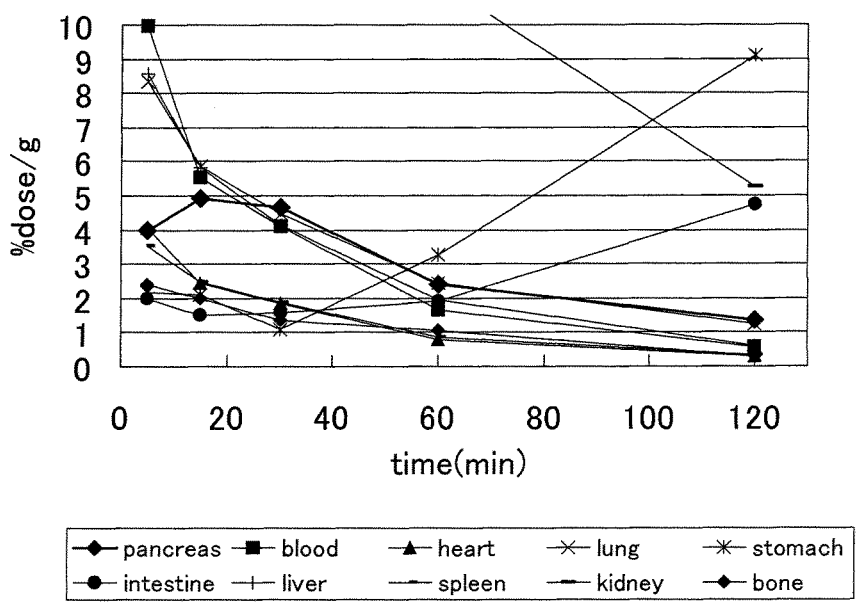
Figure 4A:
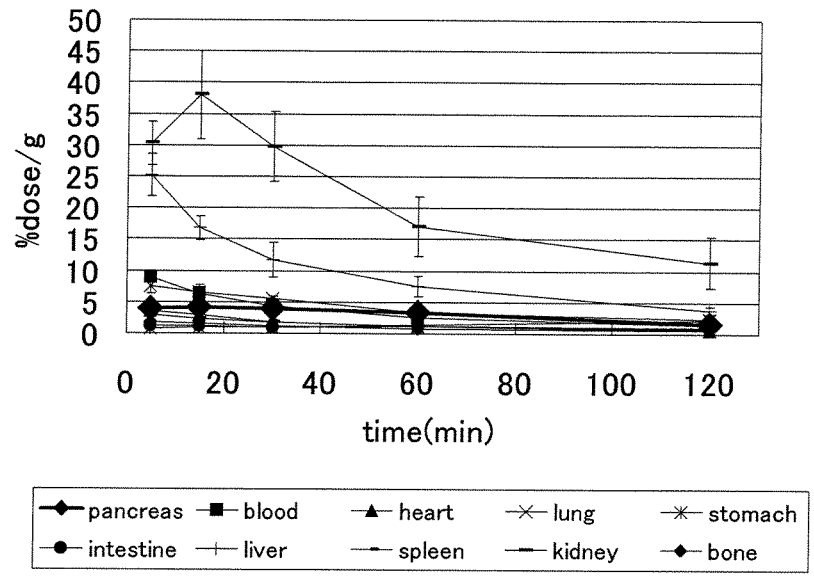
FIGS. 4A and 4B show exemplary resultant variations with time in biodistribution of a molecular probe of Reference Example 2.
Figure 4B:
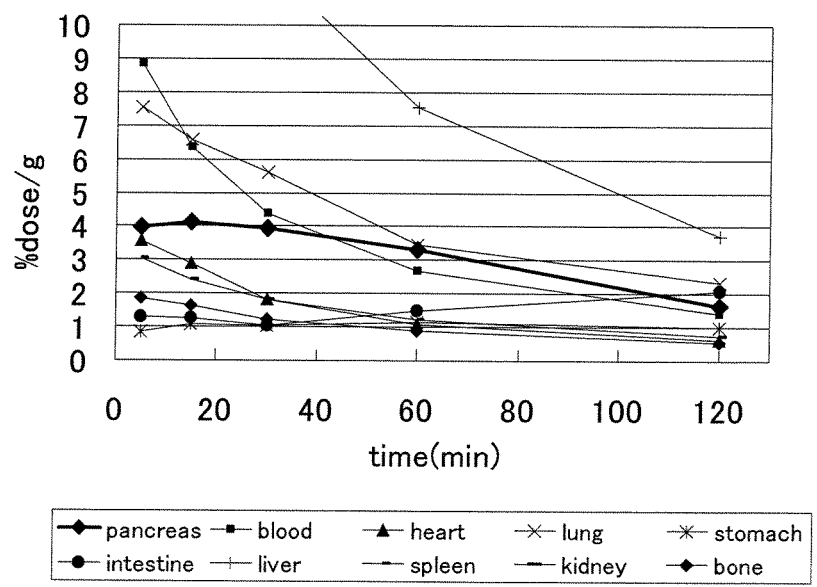

As shown in Tables 1 to 3, FIGS. 1, 3, and 4, the molecular probe prepared in Example 1, which is represented by the aforementioned formula (7), accumulated more in amount in the pancreas, and less in the liver as an organ adjacent to the pancreas, as compared with the molecular probe of Reference Example 1 represented by the aforementioned formula (11)

and the molecular probe of Reference Example 2 represented by the aforementioned formula (13). Particularly, at the point of 30 minutes after the administration and later on, the accumulation amount in the pancreas of the molecular probe of Example 1 represented by the aforementioned formula (7) was 5 times or more the accumulation amount of the molecular probe of Reference Example 1 or 2. This indicates that the molecular probe of the formula (7) prepared in Example 1 accumulated specifically in the pancreas.

By administering the molecular probe of Reference Example 1 represented by the aforementioned formula (11) to a mouse, a three-dimensional image of the pancreatic islets of the mouse was obtained. Further, by administering the molecular probe of Reference Example 2 represented by the aforementioned formula (13) to a mouse, a noninvasive three-dimensional image of the pancreatic islets of the mouse was obtained. As mentioned above, the molecular probe prepared in Example 1 represented by the aforementioned formula (7), in which a side chain of a lysine at a C-terminus was labeled, accumulated extremely much in the pancreas and accumulated less in the lever as the organ adjacent to the pancreas, in comparison with the molecular probes of Reference Examples 1 and 2 represented by the formulae (11) and (13), respectively. This suggests that the molecular probe of Example 1 enabled noninvasive three-dimensional imaging of pancreatic islets.

These results suggest that a molecular probe for imaging of the present invention enables noninvasive three-dimensional imaging of pancreas, particularly noninvasive three-dimensional imaging of pancreatic β-cells, in a human.

Based on the results of the biodistribution experiments of the molecular probe of Example 1 and the molecular probes of Reference Examples 1 and 2, the ratio of pancreas/liver (accumulation amount in pancreas/accumulation amount in liver) for each probe is shown in Table 4 below, the ratio of pancreas/kidney (accumulation amount in pancreas/accumulation amount in kidney) for each probe is shown in Table 5 below, and the ratio of pancreas/blood (accumulation amount in pancreas/accumulation amount in blood) for each probe is shown in Table 6 below.

TABLE 4

Pancreas/Liver Ratio

| | Time after administration | | | | |
|---|---|---|---|---|---|
| | 5 min | 15 min | 30 min | 60 min | 120 min |
| Ex. 1 | 10.94 | 12.58 | 20.60 | 35.87 | 45.64 |
| | (2.53) | (4.70) | (6.61) | (10.31) | (11.03) |
| Ref. Ex. 1 | 0.46 | 0.85 | 1.12 | 1.24 | 2.28 |
| Ref. Ex. 2 | 0.16 | 0.25 | 0.34 | 0.44 | 0.44 |

TABLE 5

Pancreas/Kidney Ratio

| | Time after administration | | | | |
|---|---|---|---|---|---|
| | 5 min | 15 min | 30 min | 60 min | 120 min |
| Ex. 1 | 0.25 | 0.47 | 0.92 | 1.87 | 3.66 |
| | (0.07) | (0.18) | (0.21) | (0.45) | (0.67) |
| Ref. Ex. 1 | 0.09 | 0.13 | 0.19 | 0.22 | 0.26 |
| Ref. Ex. 2 | 0.13 | 0.11 | 0.13 | 0.19 | 0.14 |

TABLE 6

Pancreas/Blood Ratio

| | Time after administration | | | | |
|---|---|---|---|---|---|
| | 5 min | 15 min | 30 min | 60 min | 120 min |
| Ex. 1 | 4.10 | 8.54 | 15.50 | 30.92 | 56.33 |
| | (1.14) | (3.26) | (4.44) | (10.43) | (12.06) |
| Ref. Ex. 1 | 0.40 | 0.89 | 1.14 | 1.47 | 2.36 |
| Ref. Ex. 2 | 0.45 | 0.65 | 0.89 | 1.25 | 1.16 |

As shown in Table 4, the ratio of pancreas/liver for the molecular probe of Example 1 represented by the formula (7) increased with time, and exceeded 10 times those for the molecular probes of Reference Examples 1 and 2 in all of the time periods. As shown in Table 5, also the ratio of pancreas/kidney for the molecular probe of the formula (7) was higher as compared with those for the molecular probes of Reference Examples 1 and 2. Further, as shown in Table 6, the ratio of pancreas/blood for the molecular probe of the formula (7) was remarkably higher as compared with those for the molecular probes of Reference Examples 1 and 2, which became 4 or greater at an early stage after the administration and indicated a satisfactory blood clearance. Thus, it is suggested that clear images of pancreas can be obtained at the time of imaging with the molecular probe of the formula (7), which has an excellent blood clearance and accumulates in pancreas in a large amount while accumulates less in the organs surrounding pancreas.

Example 2

The three-dimensional PET imaging was performed using the molecular probe prepared in Example 1 (the molecular probe of the formula (7)).

[Three-Dimensional Imaging]

The prepared molecular probe of the formula (7) (80 µCi) was administered by intravenous injection to anesthetized 6-week-old ddY mice (male, weight: 30 g), and PET images were taken with use of the following PET device under the following conditions:

Imaging device: eXplore Vista (trade name, produced by GE)

Scan mode: Static scan

Reconstruction: 2DOSEM (Dynamic OS-EM)

At a point of 10 minutes after the administration of the molecular probe of the formula (7), 100 µl of a CT contrast medium for experiment animals, "Fenestra LC" (product name, produced by GE) was administered by intravenous injection. In addition to the aforementioned PET images, CT images of the aforementioned mice were taken with use of the following CT device under the following conditions:

Imaging device: R_mCT (product name, produced by Rigaku Corporation)

Scan mode: lamp voltage (90 kV), lamp current (88 µA), set magnification ratio (4.0), scanning time (2.0 minutes)

The obtained PET image and CT image were fused using PMOD (product name, produced by PMOD Technologies, Ltd.). Exemplary results obtained are shown in FIG. 5. The images were taken at a point of 30 minutes after the administration of the molecular probe (integrating time: 15 minutes). In FIG. 5, (a) shows a transverse view, (b) shows a coronal view, and (c) shows a saggital view. In (a) to (c) of FIG. 5, a void circle indicates the position of the pancreas; in (a) of FIG. 5, void circles of dotted lines indicate the positions of the kidneys; and in (b) and (c) of FIG. 5, a void circle of an alternate long and short dashed line indicates the position of the liver. It should be noted that in (a) to (c) of FIG. 5, the degrees of contrast are at the same level.

As shown in (a) to (c) of FIG. 5, the position of the pancreas was clearly determined non-invasively, by using the molecular probe of the formula (7). In other words, it was confirmed that the non-invasive three-dimensional imaging of the pancreatic islets was enabled by the molecular probe of the present invention.

Example 3

Using a molecular probe (SEQ ID NO. 14) of the following formula (14), which has a configuration in which an amino group of a side chain of a lysine residue at position 12 is labeled with [$^{125}$I]3-iodobenzoyl group (hereinafter, referred to also as "[$^{125}$I]IB label"), a carboxyl group at a C-terminus is amidated and an α-amino group at an N-terminus is unmodified in the amino acid sequence of SEQ ID NO. 1, determination of biodistribution of the same in a mouse, blocking experiment, and a two-dimensional analysis were carried out.

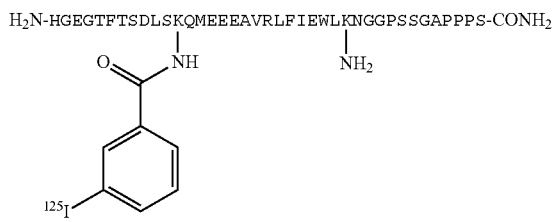

(14)

[Preparation of Probe]

The molecular probe of the formula (14) shown above was prepared in the same manner as that of Example 1 except that [$^{125}$I]N-succinimidyl 3-iodobenzoate ([$^{125}$I]SIB) was used in place of [$^{18}$F]SFB.

[Biodistribution]

The molecular probe thus prepared (0.5 μCi) of the formula (14) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice (n=5). The weight and the radioactivity of each organ were determined, and an accumulation amount (% dose/g) was calculated from the radioactivity per unit weight. Exemplary results are shown in Table 7 below and FIGS. 6A and 6B. FIG. 6A is a graph showing how the accumulation of the molecular probe in each organ varied with time, and FIG. 6B is a graph zooming in on FIG. 6A.

TABLE 7

| | Time after administration | | | | |
|---|---|---|---|---|---|
| | 5 min | 15 min | 30 min | 60 min | 120 min |
| Pancreas | 25.77 | 35.35 | 43.66 | 34.15 | 22.91 |
| | (2.26) | (2.75) | (2.28) | (3.19) | (3.61) |
| Blood | 5.41 | 3.06 | 2.20 | 1.54 | 0.76 |
| | (0.57) | (0.35) | (0.19) | (0.15) | (0.15) |
| Heart | 3.28 | 2.28 | 1.88 | 1.98 | 0.70 |
| | (0.37) | (0.56) | (0.45) | (0.42) | (0.16) |
| Lung | 94.71 | 115.99 | 143.73 | 136.51 | 84.62 |
| | (21.37) | (16.69) | (22.25) | (14.39) | (14.52) |

TABLE 7-continued

| | Time after administration | | | | |
|---|---|---|---|---|---|
| | 5 min | 15 min | 30 min | 60 min | 120 min |
| Stomach | 4.19 | 5.88 | 7.18 | 5.17 | 3.71 |
| | (1.83) | (3.43) | (1.43) | (0.50) | (2.04) |
| Intestine | 2.97 | 3.70 | 5.67 | 6.02 | 6.28 |
| | (0.47) | (0.70) | (1.11) | (0.37) | (1.59) |
| Liver | 2.45 | 3.15 | 2.92 | 2.30 | 1.36 |
| | (0.18) | (0.35) | (0.48) | (0.17) | (0.24) |
| Spleen | 2.11 | 1.52 | 1.14 | 0.86 | 0.43 |
| | (0.35) | (0.21) | (0.24) | (0.18) | (0.09) |
| Kidney | 38.22 | 33.34 | 21.31 | 13.88 | 8.32 |
| | (4.84) | (1.53) | (2.87) | (0.90) | (1.89) |
| Thyroid gland | 5.33 | 3.80 | 4.02 | 2.58 | 3.32 |
| | (0.81) | (0.98) | (0.93) | (0.74) | (1.94) |

Each numerical value indicates an average (SD) of 5 mice.

As shown in Table 7, FIGS. 6A and 6B, the accumulation of the molecular probe of the formula (14) prepared in Example 3 into the pancreas was 25.8% dose/g at a point of 5 minutes after the administration, 35.4% dose/g at a point of 15 minutes after the administration, 43.7% dose/g at a point of 30 minutes after the administration, and 34.2% dose/g at a point of 60 minutes after the administration. The ratio of pancreas/stomach was more than 6 during any of the time periods. The ratio of pancreas/intestine was reaching the vicinity of 8 during a time period from the point of 5 minutes to the point of 30 minutes after the administration. Further, during any of the time periods, the ratio of pancreas/liver exceeded 10. These results suggest that the molecular probe of the formula (14) shown above makes it possible to conduct the noninvasive three-dimensional imaging of pancreatic β-cells by SPECT, and preferably the quantification of pancreatic β-cells, not only in mice but also in humans.

Further, as shown in FIGS. 6A and 6B, no great change was seen in the accumulation of the molecular probe of the formula (14) in the thyroid gland. Therefore, the molecular probe of the formula (14) is considered suitable for the imaging of pancreatic β-cells, particularly noninvasive imaging of pancreatic β-cells.

Reference Example 3

For Reference Example 3, using a molecular probe represented by the following formula (16) (SEQ ID NO. 16), biodistribution of this molecular probe in mice was measured in the same manner as Example 1. The results are shown in Table 8 below.

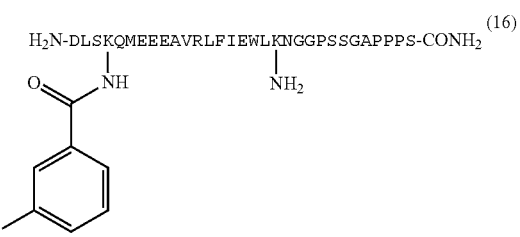

(16)

TABLE 8

| | Time after administration | | | | |
|---|---|---|---|---|---|
| | 5 min | 15 min | 30 min | 60 min | 120 min |
| Pancreas | 17.53 | 25.43 | 45.37 | 27.49 | 23.02 |
| | (3.43) | (5.09) | (5.87) | (12.49) | (4.74) |
| Blood | 9.62 | 5.73 | 4.03 | 1.84 | 1.54 |
| | (0.99) | (0.43) | (0.57) | (0.46) | (0.42) |
| Heart | 4.55 | 2.91 | 2.46 | 1.03 | 0.74 |
| | (0.29) | (0.42) | (0.19) | (0.16) | (0.08) |
| Lung | 39.67 | 51.64 | 67.29 | 44.74 | 41.21 |
| | (4.48) | (12.04) | (13.73) | (15.20) | (9.63) |
| Stomach | 2.69 | 4.24 | 9.61 | 4.08 | 11.30 |
| | (0.77) | (0.63) | (10.24) | (0.95) | (6.28) |
| Intestine | 2.24 | 2.95 | 4.36 | 3.08 | 13.16 |
| | (0.30) | (0.47) | (2.23) | (0.76) | (16.82) |
| Liver | 15.79 | 8.89 | 6.66 | 3.05 | 2.56 |
| | (0.93) | (0.98) | (0.72) | (0.69) | (0.33) |
| Spleen | 3.73 | 2.86 | 2.28 | 1.11 | 0.71 |
| | (0.62) | (0.48) | (0.54) | (0.33) | (0.16) |
| Kidney | 18.24 | 19.22 | 18.36 | 9.72 | 8.25 |
| | (1.76) | (1.73) | (4.53) | (1.35) | (1.41) |
| Thyroid gland | 4.06 | 2.91 | 2.81 | 1.63 | 2.32 |
| | (0.85) | (0.54) | (0.52) | (0.42) | (0.71) |

Each numerical value indicates an average (SD) of 5 mice.

As shown in Tables 7 and 8, the molecular probe of Example 3 represented by the formula (14) accumulated in large amount in the pancreas, as compared with the molecular probe of Reference Example 3 represented by the formula (16). Particularly, during a time period from the point of 15 minutes to the point of 60 minutes after the administration, the accumulation of the molecular probe of the formula (14) in the pancreas was maintained at a level exceeding 30% dose/g. Further, the molecular probe of the formula (14) accumulated significantly less in amount in the liver as an organ adjacent to the pancreas, as compared with the molecular probe of Reference Example 3. Thus, the molecular probe of the formula (14) is considered as having an excellent organ specificity with respect to the pancreas.

Based on the results of the biodistribution experiments of the molecular probe of Example 3 and the molecular probe of Reference Example 3, the ratio of pancreas/liver for each probe is shown in Table 9 below, the ratio of pancreas/kidney for each probe is shown in Table 10 below, and the ratio of pancreas/blood for each probe is shown in Table 11 below.

TABLE 9

| | Pancreas/Liver Ratio | | | | |
|---|---|---|---|---|---|
| | Time after administration | | | | |
| | 5 min | 15 min | 30 min | 60 min | 120 min |
| Ex. 3 | 10.53 | 11.30 | 15.35 | 14.97 | 17.38 |
| | (0.89) | (1.18) | (2.94) | (2.06) | (5.06) |
| Ref. Ex. 3 | 1.11 | 2.91 | 6.84 | 8.73 | 9.05 |
| | (0.21) | (0.71) | (0.78) | (2.21) | (1.83) |

TABLE 10

| | Pancreas/Kidney Ratio | | | | |
|---|---|---|---|---|---|
| | Time after administration | | | | |
| | 5 min | 15 min | 30 min | 60 min | 120 min |
| Ex. 3 | 0.68 | 1.06 | 2.08 | 2.47 | 2.84 |
| | (0.11) | (0.12) | (0.28) | (0.32) | (0.61) |
| Ref. Ex. 3 | 0.97 | 1.34 | 2.54 | 2.75 | 2.79 |
| | (0.21) | (0.29) | (0.42) | (0.90) | (0.30) |

TABLE 11

| | Pancreas/Blood Ratio | | | | |
|---|---|---|---|---|---|
| | Time after administration | | | | |
| | 5 min | 15 min | 30 min | 60 min | 120 min |
| Ex. 3 | 4.78 | 11.63 | 19.97 | 22.37 | 31.22 |
| | (0.38) | (1.29) | (1.84) | (3.68) | (8.21) |
| Ref. Ex. 3 | 1.84 | 4.46 | 11.34 | 14.46 | 15.26 |
| | (0.41) | (0.94) | (1.35) | (3.24) | (2.43) |

As shown in Table 9, the ratio of pancreas/liver for the molecular probe of Example 3 represented by the formula (14) increased with time, and was higher than that for the molecular probe of Reference Example 3 in all of the time periods. Although the ratio of pancreas/kidney for the molecular probe of the formula (14) was about the same level as that for the molecular probe of Reference Example 3 (see Table 10), the ratio of pancreas/blood for the molecular probe of the formula (14) was higher as compared with that for the molecular probe of Reference Example 3 (see Table 11), which became 4 or greater at an early stage after the administration and indicated a satisfactory blood clearance. Thus, it is suggested that clear images of pancreas can be obtained at the time of imaging with the molecular probe of the formula (14), which has an excellent blood clearance and accumulates in pancreas in a large amount while accumulates less in the organs surrounding pancreas.

[Blocking Experiment]

A blocking experiment was performed by using the molecular probe of the formula (14). For the mice, 6-week-old ddY mice (male, weight: 30 g) were used. First, non-labeled exendin(9-39) (cold probe, SEQ ID NO. 15) was administered (0.1 mL of 0.5 mg/mL solution) preliminarily by intravenous injection to unanesthetized mice. At a point of 30 minutes after the foregoing preliminary administration, the prepared molecular probe of the formula (14) (0.5 µCi) was administered by intravenous injection. Then, at a time of 30 minutes after the administration of the molecular probe of the formula (14), the organs were dissected out (n=5). The weight and the radioactivity of each organ were determined, and an accumulation amount (% dose/g) was calculated from the radioactivity per unit weight. Exemplary results are shown in FIGS. 7A and 7B.

(SEQ ID NO. 15)
H$_2$N-DLSKQMEEEAVRLFIEWLKNGGPSSGAPPPS-NH$_2$ (15)

As a control, without preliminary administration of a cold probe, the prepared molecular probe (0.5 µCi) of the formula (14) was administered to unanesthetized mice by intravenous injection. Then, at a time of 30 minutes after the administration, organs were dissected (n=5). The weight and the radioactivity of each organ were determined, and an accumulation amount (% dose/g) of the probe was calculated from the radioactivity per unit weight. Exemplary results are shown in FIGS. 7A and 7B, together with the exemplary results for the case including the preliminary administration.

Figure 7A:
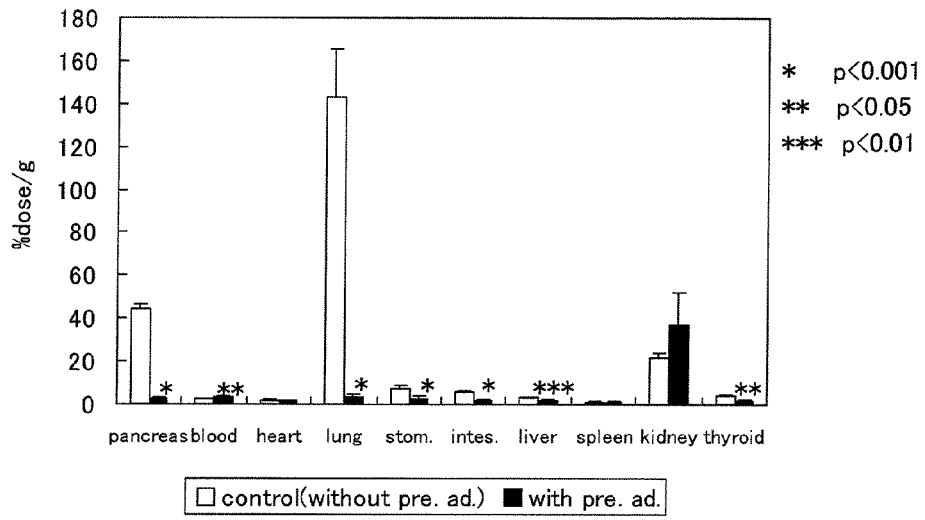
Figure 7B:
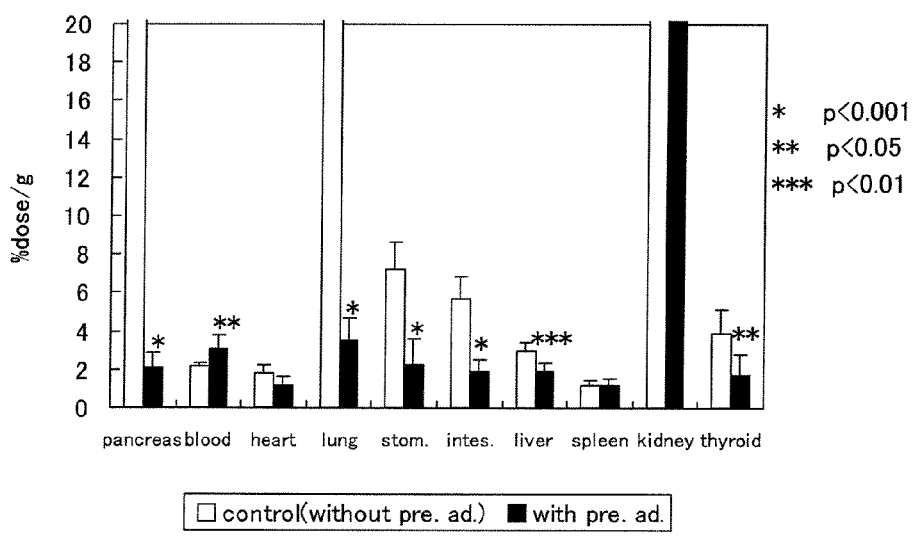

FIGS. 7A and 7B are graphs showing an example of an accumulation amount (% dose/g) for the case including the preliminary administration and an accumulation amount (% dose/g) for the control (without preliminary administration). FIG. 7B is a graph zooming in on FIG. 7A. As shown in FIGS. 7A and 7B, it was observed that the binding with a receptor was inhibited by preliminary administration of a cold probe, whereby about 95% of the uptake of the molecular probe of the formula (14) was inhibited.

[Two-Dimensional Imaging Analysis]

The molecular probe of the formula (14) (4.73 µCi) was administered to unanesthetized MIP-GFP mice (male, weight: 20 g) by intravenous injection, and at a point of 30 minutes after the administration, the pancreases were dissected out of the mice (n=2). Sections were cut out of the dissected pancreases, and each section was placed on a slide glass, covered with a cover glass. Fluorescence and radioactivity (autoradiography) of each section were determined using an image analyzer (trade name: Typhoon 9410, produced by GE Health Care Inc.) (exposure time: 18 hours). Exemplary results of the same are shown in FIG. 8.

FIG. 8 illustrates exemplary results of the imaging analysis of the pancreas sections of the MIP-GFP mice to which the molecular probe of the formula (14) was administered. The images shown therein are images showing a fluorescence signal (a) and a radioactivity signal (b) of the sections at the point of 30 minutes after the administration of the molecular probe of the formula (14).

As shown in (a) and (b) of FIG. 8, a fluorescence GFP signal and a radioactivity signal were detected, respectively, by an image analyzer in each of the pancreas sections of the MIP-GFP mice. The localization of the radioactivity signal detected from the molecular probe of the formula (14) was consistent with that of the GFP signal. From this, it was confirmed that the molecular probe of the formula (14) accumulated specifically in the pancreatic β-cells.

Next, a two-dimensional imaging analysis including the blocking process was carried out. More specifically, the fluorescence and radioactivity were measured in the same manner as described above, except that the molecular probe of the formula (14) was administered at a point of 30 minutes after the preliminary administration of non-labeled exendin(9-39) (cold probe, SEQ NO. 15). As a result, almost no radioactivity signal was detected. Thus, it was observed that a cold probe administered bound with a receptor, thereby inhibiting the uptake of the molecular probe of the formula (14) (data not shown).

From what has been described, so far, it was confirmed that the molecular probe of the formula (14) accumulated specifically in pancreatic β-cells.

Further, all of $^{125}I$, $^{123}I$, and $^{131}I$ were γ-ray emitting nuclides. Still further, $^{125}I$ and $^{123}I$ have the same numbers of nuclear spins. In view of these, it can be presumed that even a molecular probe obtained by replacing the radioactive iodine atom $^{125}I$ used in the labeling of the molecular probe of the formula (14) with $^{123}I$ or $^{131}I$ will exhibit behaviors substantially identical to those of the molecular probe of the formula (14). Further, it also can be presumed that even a molecular probe obtained by replacing the radioactive iodine atom ($^{125}I$) with $^{124}I$ will exhibit behaviors substantially identical to those of the molecular probe of the formula (14). Thus, it was suggested that using the molecular probe obtained by replacing $^{125}I$ of the molecular probe of the formula (14) with $^{123}I$, $^{124}I$, or $^{131}I$, the noninvasive three-dimensional imaging of pancreatic β-cells by SPECT, PET, or the like, for example, is enabled, and preferably, the quantification of pancreatic β-cells is enabled.

Example 4

A three-dimensional SPECT imaging analysis was carried out using a molecular probe of the following formula (17) (SEQ ID NO. 17) having a configuration in which, in the amino acid sequence of SEQ ID NO. 1, an amino group of a side chain of a lysine residue at position 12 was labeled with [$^{123}I$]3-iodobenzoyl group, a carboxyl group at a C-terminus was amidated and an α-amino group at an N-terminus was unmodified.

(17)

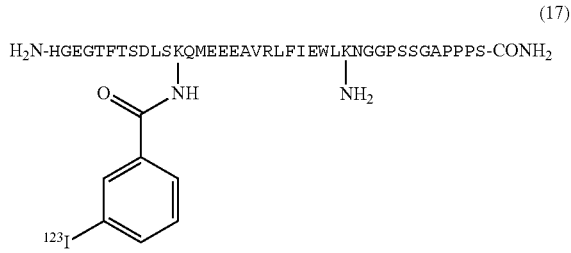

[Preparation of Molecular Probe]

Except using [$^{123}I$]N-succinimidyl 3-iodobenzoate ([$^{123}I$] SIB) in place of [$^{18}F$]SFB, the molecular probe of the formula (17) was prepared in the same manner as Example 1.

[Three-Dimensional Imaging]

Using the molecular probe of the formula (17) SPECT imaging of mice was carried out. The molecular probe of the formula (17) (172 µCi (6.36 MBq)/120 µL) was administered to 6-week-old ddY mice (male, weight: about 30 g) by intravenous injection, and then after 20 minutes from the administration of the molecular probe the mice were subjected to inhalation anesthesia with enflurane. And after 30 minutes from the administration of the molecular probe, the SPECT imaging was carried out under the following imaging conditions with use of a gamma camera (product name: SPECT 2000H-40, manufactured by Hitachi Medical Corporation). Images obtained were reconfigured under the following reconfiguration conditions.

Imaging Conditions
Collimator: LEPH pinhole collimator
Collecting range: 360°
Step angle: 11.25°
Collecting time: 40 sec per direction
  1×32 frames per 60 sec (total: 32 min)
Reconfiguration Condition
Pretreatment filter: Butterworth filter (order: 10, cutoff frequency: 0.15)

Exemplary results are shown in FIG. 9. The images shown in FIG. 9 were taken after 30 minutes from the administration of the molecular probe. Shown in FIG. 9 are, starting from the left, a transverse view, a coronal view and a sagittal view. In the coronal view of FIG. 9, the position of the pancreas is indicated by a while arrow.

As shown in FIG. 9, the position of the pancreas was confirmed noninvasively in mice with use of the molecular probe of the formula (17). In other words, it was confirmed that the molecular probe of the present invention enables the noninvasive three-dimensional imaging of the pancreas.

Thus, in view of that the position of the pancreas was confirmed noninvasively in a mouse that has the pancreas in a smaller size than that of a human and in which the organs are present more densely than in a human, this suggests that in a human that has the pancreas in a greater size than that of a mouse and in which the organs are present not as densely as in a mouse, the position of the pancreas and the size of the pancreas can be determined more clearly, and moreover, an amount of the molecular probe bonding to pancreatic β-cells can be determined.

These results suggest that the molecular probe for imaging according to the present invention enables noninvasive three-dimensional imaging of the pancreas, particularly noninvasive three-dimensional imaging of pancreatic β-cells and GLP-1R of pancreatic β-cells, in a human.

Example 5

Using a molecular probe of the following formula (18) (SEQ ID NO. 18), measurements of biodistribution of this molecular probe in mice and two-dimensional imaging analysis were carried out. The molecular probe of the formula (18) is a polypeptide represented by the first to the thirtieth amino acids of SEQ ID NO. 1 and in which the amino group of the side chain of a lysine residue at position 12 is labeled with [$^{125}$I] IB, the carboxyl group at the C-terminus is amidated, and the α-amino group at the N-terminus is unmodified.

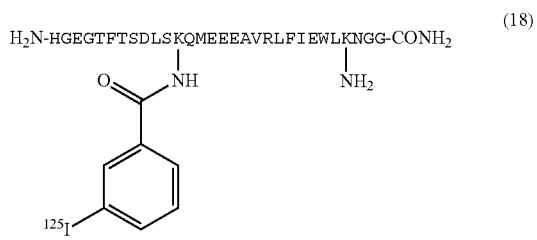

(18)

[Preparation of Molecular Probe]

Except synthesizing the polypeptide represented by the first to the thirtieth amino acids of SEQ ID NO. 1, the molecular probe of the formula (18) was prepared in the same manner as Example 3.

[Biodistribution]

The molecular probe of the formula (18) (0.69 µCi) was administered to unanesthetized 6-week-old ddY mice (male, weight: 30 g) by intravenous injection (through the tail vein). At points of 5 minutes, 15 minutes, 30 minutes, 60 minutes, and 120 minutes after the administration, organs were dissected out of the mice (n=5). The weight and the radioactivity of each organ were determined, and an accumulation amount (% dose/g) of the probe was calculated from the radioactivity per unit weight. Exemplary results are shown in Table 12 below and FIG. 10. FIG. 10 is a graph showing how the accumulation of the molecular probe of the formula (18) in each organ varied with time.

TABLE 12

| | Time after administration | | | | |
|---|---|---|---|---|---|
| | 5 min | 15 min | 5 min | 60 min | 120 min |
| Pancreas | 14.68 | 18.19 | 20.25 | 16.28 | 8.02 |
| | (1.34) | (1.80) | (1.19) | (2.31) | (1.51) |
| Blood | 14.31 | 8.53 | 4.94 | 3.11 | 1.46 |
| | (0.77) | (0.68) | (0.42) | (0.17) | (0.38) |
| Heart | 5.00 | 3.34 | 2.26 | 1.34 | 0.70 |
| | (0.36) | (0.28) | (0.18) | (0.15) | (0.20) |
| Lung | 42.07 | 34.80 | 27.84 | 17.22 | 8.19 |
| | (2.28) | (5.86) | (3.65) | (3.95) | (2.47) |
| Stomach | 1.82 | 2.61 | 2.39 | 2.02 | 1.59 |
| | (0.36) | (0.57) | (0.30) | (0.35) | (0.78) |
| Intestine | 2.99 | 4.08 | 4.60 | 6.63 | 7.65 |
| | (0.42) | (0.28) | (0.34) | (1.17) | (3.49) |
| Liver | 11.96 | 8.83 | 6.22 | 4.36 | 2.39 |
| | (0.52) | (0.51) | (0.60) | (0.31) | (0.76) |
| Spleen | 4.72 | 3.77 | 2.33 | 1.47 | 0.74 |
| | (0.41) | (0.29) | (0.21) | (0.20) | (0.17) |
| Kidney | 23.78 | 31.12 | 22.16 | 16.55 | 9.14 |
| | (2.23) | (3.03) | (2.32) | (3.41) | (2.99) |

TABLE 12-continued

| | Time after administration | | | | |
|---|---|---|---|---|---|
| | 5 min | 15 min | 5 min | 60 min | 120 min |
| Thyroid gland | 6.37 | 3.87 | 1.89 | 1.71 | 1.20 |
| | (1.36) | (0.66) | (0.40) | (1.13) | (0.64) |

Each numerical value indicates an average (SD) of 5 mice.

As shown in Table 12 and FIG. 10, the accumulation of the molecular probe of the formula (18) in the pancreas reached to a level of about 15% dose/g at an early stage after the administration, and it became the largest at the point of 30 minutes after the administration. Further, as the accumulation of the molecular probe in the thyroid gland decreased with time, this suggests that the molecular probe of the formula (18) was not subjected to deiodization metabolism in vivo.

Reference Example 4

For Reference Example 4, biodistribution of a molecular probe represented by the following formula (19) (SEQ ID NO. 19) in mice was measured in the same manner as Example 5. The amount of the molecular probe of the formula (19) administered was 0.57 µCi. The exemplary results are shown in Table 13 below and FIG. 11. FIG. 11 is a graph showing how the accumulation of the molecular probe of the formula (19) in each organ varied with time. The molecular probe of the formula (19) is a polypeptide represented by the ninth to the thirtieth amino acids of SEQ ID NO. 1 and in which the amino group of the side chain of a lysine residue at position 4 is labeled with [$^{125}$I] IB, the carboxyl group at the C-terminus is amidated, and the α-amino group at the N-terminus is unmodified.

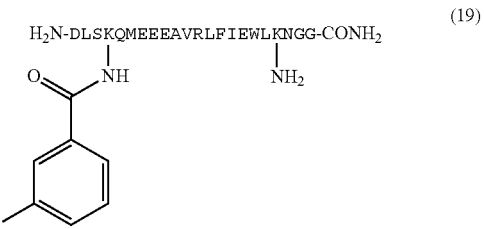

(19)

TABLE 13

| | Time after administration | | | | |
|---|---|---|---|---|---|
| | 5 min | 15 min | 5 min | 60 min | 120 min |
| Pancreas | 5.83 | 7.94 | 6.87 | 4.03 | 2.07 |
| | (1.17) | (0.97) | (1.02) | (0.63) | (0.84) |
| Blood | 11.58 | 9.92 | 6.58 | 4.35 | 2.28 |
| | (1.07) | (0.76) | (0.76) | (0.36) | (0.47) |
| Heart | 3.69 | 3.44 | 2.30 | 1.65 | 0.90 |
| | (0.27) | (0.48) | (0.28) | (0.20) | (0.18) |
| Lung | 13.55 | 12.35 | 9.12 | 5.51 | 3.18 |
| | (2.92) | (1.33) | (0.81) | (0.44) | (1.35) |
| Stomach | 1.20 | 1.16 | 1.38 | 2.05 | 1.43 |
| | (0.38) | (0.36) | (0.64) | (0.94) | (0.50) |
| Intestine | 1.43 | 1.76 | 2.60 | 4.41 | 3.86 |
| | (0.18) | (0.09) | (0.63) | (0.91) | (1.32) |
| Liver | 42.30 | 36.60 | 26.38 | 17.59 | 8.65 |
| | (3.09) | (1.97) | (0.92) | (1.37) | (2.15) |
| Spleen | 2.98 | 3.77 | 2.74 | 1.84 | 0.99 |
| | (0.22) | (0.85) | (0.38) | (0.29) | (0.19) |

TABLE 13-continued

| | Time after administration | | | | |
|---|---|---|---|---|---|
| | 5 min | 15 min | 5 min | 60 min | 120 min |
| Kidney | 8.52 | 14.20 | 14.46 | 11.00 | 6.86 |
| | (1.15) | (2.05) | (2.51) | (0.68) | (2.56) |
| Thyroid gland | 3.41 | 3.55 | 2.54 | 1.77 | 1.04 |
| | (0.73) | (1.39) | (0.66) | (0.45) | (0.36) |

Each numerical value indicates an average (SD) of 5 mice.

Based on the results of the experiments on the biodistribution of the molecular probe represented by the formula (18) of Example 5 and the molecular probes of Reference Examples 3 and 4, the ratio of pancreas/liver for each probe is shown in Table 14 below, the ratio of pancreas/kidney for each probe is shown in Table 15 below, and the ratio of pancreas/blood for each probe is shown in Table 16 below.

TABLE 14

Pancreas/Liver Ratio

| | Time after administration | | | | |
|---|---|---|---|---|---|
| | 5 min | 15 min | 30 min | 60 min | 120 min |
| Ex. 5 | 1.23 | 2.06 | 3.29 | 3.73 | 3.58 |
| | (0.12) | (0.20) | (0.41) | (0.50) | (0.98) |
| Ref. Ex. 4 | 0.14 | 0.22 | 0.26 | 0.23 | 0.23 |
| | (0.02) | (0.02) | (0.04) | (0.03) | (0.06) |
| Ref. Ex. 3 | 1.11 | 2.91 | 6.84 | 8.73 | 9.05 |
| | (0.21) | (0.71) | (0.78) | (2.21) | (1.83) |

TABLE 15

Pancreas/Kidney Ratio

| | Time after administration | | | | |
|---|---|---|---|---|---|
| | 5 min | 15 min | 30 min | 60 min | 120 min |
| Ex. 5 | 0.62 | 0.59 | 0.92 | 1.01 | 0.92 |
| | (0.05) | (0.05) | (0.12) | (0.25) | (0.19) |
| Ref. Ex. 4 | 0.68 | 0.57 | 0.49 | 0.37 | 0.30 |
| | (0.08) | (0.10) | (0.10) | (0.05) | (0.05) |
| Ref. Ex. 3 | 0.97 | 1.34 | 2.54 | 2.75 | 2.79 |
| | (0.21) | (0.29) | (0.42) | (0.90) | (0.30) |

TABLE 16

Pancreas/Blood Ratio

| | Time after administration | | | | |
|---|---|---|---|---|---|
| | 5 min | 15 min | 30 min | 60 min | 120 min |
| Ex. 5 | 1.03 | 2.14 | 4.13 | 5.23 | 5.63 |
| | (0.09) | (0.21) | (0.50) | (0.69) | (0.83) |
| Ref. Ex. 4 | 0.50 | 0.80 | 1.05 | 0.92 | 0.87 |
| | (0.07) | (0.12) | (0.17) | (0.11) | (0.23) |
| Ref. Ex. 3 | 1.84 | 4.46 | 11.34 | 14.46 | 15.26 |
| | (0.41) | (0.94) | (1.35) | (3.24) | (2.43) |

As shown in Tables 14 to 16, in the case of the molecular probe represented by the formula (18), the ratio of pancreas/liver, the ratio of pancreas/kidney and the ratio of pancreas/blood increased with time, and the ratio of pancreas/liver and the ratio of pancreas/blood became more than 2 at the point of 15 minutes after the administration. Thus, it is suggested that clear images of pancreatic β-cells can be obtained when imaging them with the molecular probe represented by the formula (18) that has an excellent blood clearance and accumulates less in the organs surrounding pancreas.

[Two-Dimensional Imaging Analysis]

The molecular probe represented by the formula (18) (5 µCi/100 µL) was administered to unanesthetized MIP-GFP mice (male, weight: about 20 g) by intravenous injection. At points of 30 minutes and 60 minutes after the administration, the pancreas was dissected out of each mouse (n=2). Sections were cut out of the dissected pancreases, and each section was placed on a slide glass, covered with a cover glass. Fluorescence and radioactivity (autoradiography) of each section were determined using an image analyzer (trade name: Typhoon 9410, produced by GE Health Care Inc.) (exposure time: 19 hours). Exemplary results are shown in FIG. 12.

Further, non-labeled exendin(9-39) (cold probe, SEQ NO. 15) was administered (50 µg/100 µL) preliminarily by intravenous injection to unanesthetized MIP-GFP mice (male, weight: 20 g). At a point of 30 minutes after the preliminary administration, the molecular probe represented by the formula (18) (5 µCi/100 µL) was administered to the mice by intravenous injection. Then, at points of 30 minutes and 60 minutes after the administration of the molecular probe represented by the formula (18), the pancreases were dissected out of each mouse (n=2). Sections were cut out of the dissected pancreases, and fluorescence and radioactivity of each section were determined in the same manner as described above. Exemplary results are shown in FIG. 12 together with the results of the case without blocking (no preliminary administration).

FIG. 12 shows images showing exemplary results of image analysis of the pancreas sections of the MIP-GFP mice to which the molecular probe represented by the formula (18) was administered. The upper images show a fluorescent signal and the lower images show a radioactivity signal of the molecular probe represented by the formula (18). In FIG. 12, the images with "+" in the Cold column show the results of the case where the cold probe was as administered prior to the administration of the molecular probe represented by the formula (18) and the images with "−" in the Cold column show the results of the case where the molecular probe represented by the formula (18) was administered without preliminarily administering the cold probe.

As shown in FIG. 12, a fluorescence GFP signal and a radioactivity signal were detected by the inn age analyzer from the pancreas sections of the MIP-GFP mice. Further, the localization of the radioactivity signal of the molecular probe represented by the formula (18) was nearly consistent with that of the GFP signal. From this, it was confirmed that the molecular probe represented by the formula (18) accumulated specifically in the pancreatic β-cells. Further, as a result of blocking the receptor by preliminarily administrating the cold probe, the radioactivity signal of the molecular probe represented by the formula (18) was hardly detected. Thus, it was suggested that the molecular probe represented by the formula (18) accumulated specifically in GLP-1R of the pancreatic β-cells.

Therefore, it is suggested that, similarly to the molecular probe represented by the formula (14) (the molecular probe of Example 3), the use of the molecular probe represented by the formula (18) having a [123/124/311I] iodine atom in place of a [$^{125}$I] iodine atom allows the noninvasive three-dimensional imaging of GLP-1R of pancreatic β-cells by SPECT, PET, or the like, and preferably, the quantification of GLP-1R of pancreatic β-cells.

As described above, the present invention is useful in, for example, the medical field, the molecule imaging field, and the field relating to diabetes.

Sequence Listing Free Text

SEQ ID NO. 1: an amino acid sequence of a molecular probe for imaging of the present invention SEQ ID NO. 2: an amino acid sequence of a molecular probe for imaging of the present invention SEQ ID NO. 3: an amino acid sequence of a molecular probe for imaging of the present invention SEQ ID NO. 4: an amino acid sequence of a precursor of a molecular probe for aging of the present invention SEQ ID NO. 5: an amino acid sequence of a precursor of a molecular probe for imaging of the present invention SEQ ID NO. 6: an amino acid sequence of a precursor of a molecular probe for imaging of the present invention SEQ ID NO. 7: an amino acid sequence of a molecular probe for imaging of Example 1

SEQ ID NO. 8: an amino acid sequence of polypeptide used for producing a molecular probe for imaging of Example 1

SEQ NO. 9: an amino acid sequence of a molecular probe precursor used for producing a molecular probe for imaging of Example 1

SEQ NO. 10: an amino acid sequence of a molecular probe precursor of Reference Example 1

SEQ ID NO. 11: an amino acid sequence of a molecular probe of Reference Example 1

SEQ NO. 12: an amino acid sequence of a molecular probe precursor of Reference Example 2

SEQ ID NO. 13: an amino acid sequence of a molecular probe of Reference Example 2

SEQ ID NO. 14: an amino acid sequence of a molecular probe for imaging of Example 3

SEQ ID NO. 15: an amino acid sequence of exendin(9-39)

SEQ NO. 16: an amino acid sequence of a molecular probe of Reference Example 3

SEQ ID NO. 17: an amino acid sequence of a molecular probe for imaging of Example 4

SEQ ID NO. 18: an amino acid sequence of a molecular probe for imaging of Example 5

SEQ ID NO. 19: an amino acid sequence of a molecular probe of Reference Example 4

SEQ ID NO. 20: an amino acid sequence of polypeptide used in the method for producing a molecular probe for imaging of the present invention The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

What is claimed is:

1. A molecular probe comprising any one of the following polypeptides:

a polypeptide represented by the following formula (1), (2), or (3);

a polypeptide that is obtained by deletion, insertion, or substitution of one, two or three amino acids with respect to the polypeptide represented by the following formula (1), (2), or (3) and binds to pancreatic islets; and a polypeptide that has a sequence identity of 85% or higher with the amino acid sequence of the polypeptide represented by the following formula (1), (2), or (3) and binds to pancreatic islets:

Z-HGEGTFTSDLSXQMEEEAVRLFIEWLKNGGPSSGAPPPS-NH$_2$ (1) (SEQ ID NO. 1)

Z-HGEGTFTSDLSKQMEEEAVRLFIEWLXNGGPSSGAPPPS-NH$_2$ (2) (SEQ ID NO. 2)

B-HGEGTFTSDLSKQMEEEAVRLFIEWLKNGGPSSGAPPPS-NH$_2$ (3) (SEQ ID NO. 3)

wherein in the formulae (1) and (2),

"X" represents a lysine residue, an amino group of a side chain of the lysine residue being labeled with a radioactive nuclide, and "Z—" indicates that an α-amino group at an N-terminus is not modified, or is modified with a modifying group having no electric charge, in the formula (3), "B—" indicates that an α-amino group at an N-terminus is labeled with a radioactive nuclide, and in the formulae (1), (2), and (3), "—NH$_2$" indicates that a carboxyl group at a C-terminus is amidated.

2. The molecular probe according to claim 1, wherein the radioactive nuclide is $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, or $^{186}$Re.

3. The molecular probe according to claim 1, wherein the amino group of the side chain of the lysine labeled with the radioactive nuclide is bonded to a group represented by a formula (I) shown below,

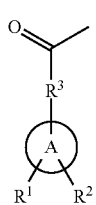

(I)

wherein
- A represents an aromatic hydrocarbon group or an aromatic heterocyclic group,
- $R^1$ represents a substituent that contains a radioactive nuclide,
- $R^2$ represents either a hydrogen atom, or one or more substituents different from that represented by $R^1$, and
- $R^3$ represents any one of a bond, an alkylene group having 1 to 6 carbon atoms, and an oxyalkylene group having 1 to 6 carbon atoms.

4. A kit for imaging of pancreatic islets, the kit comprising at least one selected from the group consisting of the molecular probe according to claim 1 and the precursor polypeptide comprising any one of the following polypeptides:
- a polypeptide represented by the following formula (4), (5), or (6);
- a polypeptide that is obtained by deletion, insertion, or substitution of one, two or three amino acids with respect to the polypeptide represented by the following formula (4), (5), or (6) and that binds to pancreatic islets after being labeled and deprotected; and
- a polypeptide that has a sequence identity of 85% or higher with the amino acid sequence of polypeptide represented by the following formula (4), (5), or (6) and binds to pancreatic islets after being labeled and deprotected:

```
                                           (SEQ ID NO. 4)
*-HGEGTFTSDLSKQMEEEAVRLFIEWLK*NGGPSSGAPPPS-NH2  (4)
                                           (SEQ ID NO. 5)
*-HGEGTFTSDLSK*QMEEEAVRLFIEWLKNGGPSSGAPPPS-NH2  (5)
                                           (SEQ ID NO. 6)
HGEGTFTSDLSK*QMEEEAVRLFIEWLK*NGGPSSGAPPPS-NH2  (6)
``` wherein
- in the formulae (4) and (5),
- "*-" indicates that an α-amino group at an N-terminus is protected by a protecting group, or is modified with a modifying group having no electric charge,
- in the formulae (4), (5), and (6),
- "K*" indicates that an amino group of a side chain of a lysine is protected by a protecting group,
- the functional groups of the side chains of the amino acids except for K* are not protected by a protecting group, and
- "—$NH_2$" indicates that a carboxyl group at a C-terminus is amidated.

5. The kit according to claim 4, wherein the molecular probe included in the kit is in a form of a parenteral solution.

6. A reagent for imaging of pancreatic islets, the reagent comprising the molecular probe according to claim 1.

7. A method of imaging pancreatic islets, the method comprising detecting a signal of the molecular probe according to claim 1 from an analyte to which the molecular probe has been administered.

8. The method of imaging according to claim 7, further comprising reconfiguring the detected signal to convert the signal into an image, and displaying the image.

9. The method of imaging pancreatic islets according to claim 7, the method further comprising determining a state of pancreatic islets on the basis of results of the imaging of pancreatic islets using the molecular probe.

10. A method of determining an amount of pancreatic islets, the method comprising:
- detecting a signal of the molecular probe according to claim 1 from an analyte to which the molecular probe has been administered; and
- calculating the amount of pancreatic islets from the detected signal of the molecular probe.

11. The method of determining an amount according to claim 10, further comprising presenting the calculated amount of pancreatic islets.

12. The molecular probe according to claim 1, wherein the molecular probe comprises the polypeptide represented by the formula (1), (2), or (3).

13. The molecular probe according to claim 1, wherein the molecular probe consists of the polypeptide represented by the formula (1), (2), or (3).

14. The molecular probe according to claim 1, wherein the molecular probe comprises a polypeptide that is obtained by deletion, insertion, or substitution of one amino acid with respect to the polypeptide represented by the formula (1), (2), or (3).

15. The molecular probe according to claim 1, wherein the molecular probe comprises a polypeptide that is obtained by deletion, insertion, or substitution of two amino acids with respect to the polypeptide represented by the formula (1), (2), or (3).

16. The molecular probe according to claim 1, wherein the molecular probe comprises a polypeptide that has sequence identity of 95% or higher with the amino acid sequence of the polypeptide represented by the following formula (1), (2), or (3).

17. A precursor polypeptide comprising any one of the following polypeptides:
- a polypeptide represented by the following formula (4), (5), or (6);
- a polypeptide that is obtained by deletion, insertion, or substitution of one, two or three amino acids with respect to the polypeptide represented by the following formula (4), (5), or (6) and binds to pancreatic islets after being labeled and deprotected; and
- a polypeptide that has a sequence identity of 85% or higher with the amino acid sequence of polypeptide represented by the following formula (4), (5), or (6) and binds to pancreatic islets after being labeled and deprotected:

```
                                           (SEQ ID NO. 4)
*-HGEGTFTSDLSKQMEEEAVRLFIEWLK*NGGPSSGAPPPS-NH2  (4)
                                           (SEQ ID NO. 5)
*-HGEGTFTSDLSK*QMEEEAVRLFIEWLKNGGPSSGAPPPS-NH2  (5)
                                           (SEQ ID NO. 6)
HGEGTFTSDLSK*QMEEEAVRLFIEWLK*NGGPSSGAPPPS-NH2  (6)
``` wherein
- in the formulae (4) and (5),
- "*-" indicates that an α-amino group at an N-terminus is protected by a protecting group, or is modified with a modifying group having no electric charge,
- in the formulae (4), (5), and (6),
- "K*" indicates that an amino group of a side chain of a lysine is protected by a protecting group, the functional groups of the side chains of the amino acids except for K* are not protected by a protecting group, and "—NH$_2$" indicates that a carboxyl group at a C-terminus is amidated.

18. A method of producing a molecular probe for imaging, the method comprising:

labeling and deprotecting the precursor polypeptide according to claim 17.

19. The method according to claim 18, wherein the labeling of the precursor polypeptide includes labeling the precursor polypeptide, using a compound containing a radioactive nuclide of $^{11}$C, $^{13}$N, $^{15}$O, $^{18}$F, $^{64}$Cu, $^{67}$Ga, $^{68}$Ga, $^{75}$Br, $^{76}$Br, $^{77}$Br, $^{99m}$Tc, $^{111}$In, $^{123}$I, $^{124}$I, $^{125}$I, $^{131}$I, or $^{186}$Re.

20. The method according to claim 18, wherein the labeling of the precursor polypeptide includes labeling the precursor polypeptide, using a compound having a group represented by the following formula (I),

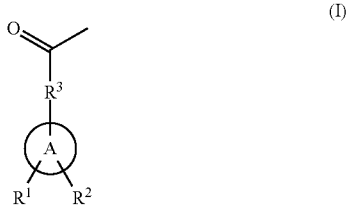

(I)

wherein

A represents an aromatic hydrocarbon group or an aromatic heterocyclic group,

R$^1$ represents a substituent that contains a radioactive nuclide,

R$^2$ represents either a hydrogen atom, or one or more substituents different from that represented by R$^1$, and R$^3$ represents any one of a bond, an alkylene group having 1 to 6 carbon atoms, and an oxyalkylene group having 1 to 6 carbon atoms.

21. The precursor polypeptide according to claim 17, wherein the precursor polypeptide comprises a polypeptide represented by the formula (4), (5), or (6).

22. The precursor polypeptide according to claim 17, wherein the precursor consists of a polypeptide represented by the formula (4), (5), or (6).

23. The precursor polypeptide according to claim 17, wherein the precursor polypeptide comprises a polypeptide that is obtained by deletion, insertion, or substitution of one amino acid of any of the polypeptides represented by the formula (4), (5), or (6).

24. The precursor polypeptide according to claim 17, wherein the precursor polypeptide comprises a polypeptide that is obtained by deletion, insertion, or substitution of two amino acids of any of the polypeptides represented by the formula (4), (5), or (6).

25. The precursor polypeptide according to claim 17, wherein the precursor polypeptide comprises a polypeptide that has a sequence identity of 95% or higher with the amino acid sequence of any of the polypeptides represented by the following formula (4), (5), or (6).

\* \* \* \* \*

SEQUENCE LISTING

```
<160> NUMBER OF SEQ ID NOS: 20

<210> SEQ ID NO 1
<211> LENGTH: 39
<212> TYPE: PRT
<213> ORGANISM: Artificial Sequence
<220> FEATURE:
<223> OTHER INFORMATION: Synthetic molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is not
      modified or is modified by a modified group.
<220> FEATURE:
<221> NAME/KEY: MOD_RES
<222> LOCATION: (12)..(12)
<223> OTHER INFORMATION: An amino group of a side chain is labeled.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Synthetic molecular probe for imaging of
      pancreatic islets
<220> FEATURE:
<221> NAME/KEY: MOD_RES
<222> LOCATION: (1)..(1)
```

-continued

```
<223> OTHER INFORMATION: An alpha-amino group of an N-terminus is not
      modified or is modified by a modified group.
<220> FEATURE:
<221> NAME/KEY: MOD_RES
<222> LOCATION: (27)..(27)
<223> OTHER INFORMATION: An amino group of a side chain is labeled.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Synthetic molecular probe for imaging of
      pancreatic islets
<220> FEATURE:
<221> NAME/KEY: MOD_RES
<222> LOCATION: (1)..(1)
<223> OTHER INFORMATION: An alpha-amino group of an N-terminus is
      labeled.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Synthetic precursor of a molecular probe for
      imaging of pancreatic islets
<220> FEATURE:
<221> NAME/KEY: MOD_RES
<222> LOCATION: (1)..(1)
<223> OTHER INFORMATION: An alpha-amino group of an N-terminus is
      protected by a protecting group or is modified by a modified
      group.
<220> FEATURE:
<221> NAME/KEY: MOD_RES
<222> LOCATION: (27)..(27)
<223> OTHER INFORMATION: An amino group of a side chain is protected
      by a protecting group.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 4

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Synthetic precursor of a molecular probe for
      imaging of pancreatic islets
<220> FEATURE:
<221> NAME/KEY: MOD_RES
<222> LOCATION: (1)..(1)
<223> OTHER INFORMATION: An amino group of an N-terminus is protected
      by a protecting group or is modified by a modified group.
<220> FEATURE:
<221> NAME/KEY: MOD_RES
<222> LOCATION: (12)..(12)
<223> OTHER INFORMATION: An amino group of a side chain is protected by
      a protecting group.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 5

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 6
<211> LENGTH: 39
<212> TYPE: PRT
<213> ORGANISM: Artificial Sequence
<220> FEATURE:
<223> OTHER INFORMATION: Synthetic precursor of a molecular probe for
      imaging of pancreatic islets
<220> FEATURE:
<221> NAME/KEY: MOD_RES
<222> LOCATION: (12)..(12)
<223> OTHER INFORMATION: An amino group of a side chain is protected by
      a protecting group.
<220> FEATURE:
<221> NAME/KEY: MOD_RES
<222> LOCATION: (27)..(27)
<223> OTHER INFORMATION: An amino group of a side chain is protected by
      a protecting group.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 7
<211> LENGTH: 39
<212> TYPE: PRT
```

-continued

<213> ORGANISM: Artificial Sequence
<220> FEATURE:
<223> OTHER INFORMATION: Synthetic molecular probe for imaging of
      pancreatic islets of Example 1
<220> FEATURE:
<221> NAME/KEY: MOD_RES
<222> LOCATION: (12)..(12)
<223> OTHER INFORMATION: An amino group of a side chain is labeled by
      [18F]fluorobenzoyl.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 7

His Gly Glu Gly Thr Phe Thr Ser Asp Leu Ser Lys Gln Met Glu Glu
 1               5                  10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 8
<211> LENGTH: 39
<212> TYPE: PRT
<213> ORGANISM: Artificial Sequence
<220> FEATURE:
<223> OTHER INFORMATION: Synthetic polypeptide for preparation of
      precursor of a molecular probe for imaging of pancreatic islets
      of Example 1
<220> FEATURE:
<221> NAME/KEY: MOD_RES
<222> LOCATION: (1)..(1)
<223> OTHER INFORMATION: An alpha-amino group of an N-terminus is
      protected by a Fmoc. A functional group of a side chain is
      protected by a Trt.
<220> FEATURE:
<221> NAME/KEY: MOD_RES
<222> LOCATION: (3)..(3)
<223> OTHER INFORMATION: A functional group of a side chain is
      protected by a OBu.
<220> FEATURE:
<221> NAME/KEY: MOD_RES
<222> LOCATION: (8)..(8)
<223> OTHER INFORMATION: A functional group of a side chain is
      protected by a OBu.
<220> FEATURE:
<221> NAME/KEY: MOD_RES
<222> LOCATION: (9)..(9)
<223> OTHER INFORMATION: A functional group of a side chain is
      protected by a OBu.
<220> FEATURE:
<221> NAME/KEY: MOD_RES
<222> LOCATION: (11)..(11)
<223> OTHER INFORMATION: A functional group of a side chain is
      protected by a OBu.
<220> FEATURE:
<221> NAME/KEY: MOD_RES
<222> LOCATION: (12)..(12)
<223> OTHER INFORMATION: An amino group of a side chain is protected by
      a Mmt.
<220> FEATURE:
<221> NAME/KEY: MOD_RES
<222> LOCATION: (13)..(13)
<223> OTHER INFORMATION: A functional group of a side chain is protected
      by a Trt.
<220> FEATURE:
<221> NAME/KEY: MOD_RES
<222> LOCATION: (15)..(17)
<223> OTHER INFORMATION: A functional group of a side chain is protected
      by a OBu.
<220> FEATURE:
<221> NAME/KEY: MOD_RES
<222> LOCATION: (20)..(20)
<223> OTHER INFORMATION: A functional group of a side chain is protected

```
        by a Pdf.
<220> FEATURE:
<221> NAME/KEY: MOD_RES
<222> LOCATION: (24)..(24)
<223> OTHER INFORMATION: A functional group of a side chain is protected
        by a OBu.
<220> FEATURE:
<221> NAME/KEY: MOD_RES
<222> LOCATION: (25)..(25)
<223> OTHER INFORMATION: A functional group of a side chain is protected
        by a Boc.
<220> FEATURE:
<221> NAME/KEY: MOD_RES
<222> LOCATION: (27)..(27)
<223> OTHER INFORMATION: An amino group of a side chain is protected by
        a Mmt.
<220> FEATURE:
<221> NAME/KEY: MOD_RES
<222> LOCATION: (28)..(28)
<223> OTHER INFORMATION: A functional group of a side chain is protected
        by a Trt.
<220> FEATURE:
<221> NAME/KEY: MOD_RES
<222> LOCATION: (32)..(33)
<223> OTHER INFORMATION: A functional group of a side chain is protected
        by a OBu.
<220> FEATURE:
<221> NAME/KEY: MOD_RES
<222> LOCATION: (39)..(39)
<223> OTHER INFORMATION: A functional group of a side chain is protected
        by a OBu.

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic precursor of a molecular probe for
        imaging of pancreatic islets of Example 1
<220> FEATURE:
<221> NAME/KEY: MOD_RES
<222> LOCATION: (1)..(1)
<223> OTHER INFORMATION: An alpha-amino group of an N-terminus is
        protected by a Fmoc.
<220> FEATURE:
<221> NAME/KEY: MOD_RES
<222> LOCATION: (27)..(27)
<223> OTHER INFORMATION: An amino group of a side chain is protected by
        a Fmoc.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 9

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 10
```

```
<211> LENGTH: 31
<212> TYPE: PRT
<213> ORGANISM: Artificial Sequence
<220> FEATURE:
<223> OTHER INFORMATION: Synthetic precursor of a molecular probe of
      reference example 1
<220> FEATURE:
<221> NAME/KEY: MOD_RES
<222> LOCATION: (1)..(1)
<223> OTHER INFORMATION: An alpha-amino group of an N-terminus is
      protected by a Fmoc.
<220> FEATURE:
<221> NAME/KEY: MOD_RES
<222> LOCATION: (19)..(19)
<223> OTHER INFORMATION: An amino group of a side chain is protected by
      a Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 10

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: Synthetic molecular probe of reference example
      1
<220> FEATURE:
<221> NAME/KEY: MOD_RES
<222> LOCATION: (4)..(4)
<223> OTHER INFORMATION: An amino group of a side chain is labeled by
      [18F]fluorobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 11

Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: Synthetic precursor of a molecular probe of
      reference example 2
<220> FEATURE:
<221> NAME/KEY: MOD_RES
<222> LOCATION: (1)..(1)
<223> OTHER INFORMATION: An alpha-amino group of an N-terminus is
      protected by a Fmoc.
<220> FEATURE:
<221> NAME/KEY: MOD_RES
<222> LOCATION: (4)..(4)
<223> OTHER INFORMATION: Amino group of side chain is protected by a
      Fmoc.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 12
```

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 13
<211> LENGTH: 31
<212> TYPE: PRT
<213> ORGANISM: Artificial Sequence
<220> FEATURE:
<223> OTHER INFORMATION: Synthetic molecular probe of reference example
      2
<220> FEATURE:
<221> NAME/KEY: MOD_RES
<222> LOCATION: (19)..(19)
<223> OTHER INFORMATION: An amino group of a side chain is labeled by
      [18F]fluorobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 13

```
Asp Leu Ser Lys Gln Met Glu Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 14
<211> LENGTH: 39
<212> TYPE: PRT
<213> ORGANISM: Artificial Sequence
<220> FEATURE:
<223> OTHER INFORMATION: Synthetic molecular probe for imaging of
      pancreatic islets of Example 3
<220> FEATURE:
<221> NAME/KEY: MOD_RES
<222> LOCATION: (12)..(12)
<223> OTHER INFORMATION: An amino group of a side chain is labeled by
      [125I]3-iodobenzoyl.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 14

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
            35
```

<210> SEQ ID NO 15
<211> LENGTH: 31
<212> TYPE: PRT
<213> ORGANISM: Artificial Sequence
<220> FEATURE:
<223> OTHER INFORMATION: Synthetic sequence of Exendin-(9-39)
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 15

```
Asp Leu Ser Lys Gln Met Glu Glu Glu Ala Val Arg Leu Phe Ile Glu
1               5                   10                  15
```

```
Trp Leu Lys Asn Gly Gly Pro Ser Ser Gly Ala Pro Pro Pro Ser
            20                  25                  30
```

<210> SEQ ID NO 16
<211> LENGTH: 31
<212> TYPE: PRT
<213> ORGANISM: Artificial Sequence
<220> FEATURE:
<223> OTHER INFORMATION: Synthetic molecular probe of reference example
      3
<220> FEATURE:
<221> NAME/KEY: MOD_RES
<222> LOCATION: (4)..(4)
<223> OTHER INFORMATION: An amino group of a side chain is labeled by
      [125I]3-iodobenzoyl.
<220> FEATURE:
<221> NAME/KEY: MOD_RES
<222> LOCATION: (31)..(31)
<223> OTHER INFORMATION: A carboxyl group of a C-terminus is amidated.

<400> SEQUENCE: 16

```
Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30
```

<210> SEQ ID NO 17
<211> LENGTH: 39
<212> TYPE: PRT
<213> ORGANISM: Artificial Sequence
<220> FEATURE:
<223> OTHER INFORMATION: Synthetic molecular probe for imaging of
      pancreatic islets of Example 4
<220> FEATURE:
<221> NAME/KEY: MOD_RES
<222> LOCATION: (12)..(12)
<223> OTHER INFORMATION: An amino group of a side chain is labeled by
      [123I]3-iodobenzoyl.
<220> FEATURE:
<221> NAME/KEY: MOD_RES
<222> LOCATION: (39)..(39)
<223> OTHER INFORMATION: A carboxyl group of a C-terminus is amidated.

<400> SEQUENCE: 17

```
His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35
```

<210> SEQ ID NO 18
<211> LENGTH: 30
<212> TYPE: PRT
<213> ORGANISM: Artificial Sequence
<220> FEATURE:
<223> OTHER INFORMATION: Synthetic molecular probe for imaging of
      pancreatic islets of Example 4
<220> FEATURE:
<221> NAME/KEY: MOD_RES
<222> LOCATION: (12)..(12)
<223> OTHER INFORMATION: An amino group of a side chain is labeled by
      [125I]3-iodobenzoyl.
<220> FEATURE:
<221> NAME/KEY: MOD_RES
<222> LOCATION: (30)..(30)
<223> OTHER INFORMATION: A carboxyl group of a C-terminus is amidated.

<400> SEQUENCE: 18

```
His Gly Glu Gly Thr Phe Thr Ser Asp Leu Ser Lys Gln Met Glu Glu
```

```
                1               5                  10                  15
Glu Ala Val Arg Leu Phe Ile Glu Trp Leu Lys Asn Gly Gly
                    20                  25                  30

<210> SEQ ID NO 19
<211> LENGTH: 22
<212> TYPE: PRT
<213> ORGANISM: Artificial Sequence
<220> FEATURE:
<223> OTHER INFORMATION: Synthetic molecular probe of reference example
      4
<220> FEATURE:
<221> NAME/KEY: MOD_RES
<222> LOCATION: (4)..(4)
<223> OTHER INFORMATION: An amino group of a side chain is labeled by
      [125I]3-iodobenzoyl.
<220> FEATURE:
<221> NAME/KEY: MOD_RES
<222> LOCATION: (22)..(22)
<223> OTHER INFORMATION: A carboxyl group of a C-terminus is amidated.

<400> SEQUENCE: 19

Asp Leu Ser Lys Gln Met Glu Glu Glu Ala Val Arg Leu Phe Ile Glu
1               5                  10                  15

Trp Leu Lys Asn Gly Gly
            20

<210> SEQ ID NO 20
<211> LENGTH: 39
<212> TYPE: PRT
<213> ORGANISM: Artificial sequence
<220> FEATURE:
<223> OTHER INFORMATION: Synthetic polypeptide for use preparation of
      imaging probe for pancreatic islets

<400> SEQUENCE: 20

His Gly Glu Gly Thr Phe Thr Ser Asp Leu Ser Lys Gln Met Glu Glu
1               5                  10                  15

Glu Ala Val Arg Leu Phe Ile Glu Trp Leu Lys Asn Gly Gly Pro Ser
                    20                  25                  30

Ser Gly Ala Pro Pro Pro Ser
            35
```